United States Patent
Greco et al.

(10) Patent No.: US 10,844,045 B2
(45) Date of Patent: Nov. 24, 2020

(54) PHARMACEUTICAL SALTS N-(2-(2-(DIMETHYLAMINO)ETHOXY)-4-METHOXY-5-((4-(1-METHYL-1H-INDOL-3-YL)PYRIMIDIN-2-YL)AMINO)PHENYL) ACRYLAMIDE AND CRYSTALLINE FORMS THEREOF

(71) Applicant: Beta Pharma, Inc., Wilmington, DE (US)

(72) Inventors: Michael N. Greco, Lansdale, PA (US); Michael J. Costanzo, Warminster, PA (US); Michael A. Green, Easton, PA (US); Jirong Peng, Mequon, WI (US); Victoria Lynn Wilde, Montclair, NJ (US); Don Zhang, Princeton, NJ (US)

(73) Assignee: BETA PHARMA, INC., Wilmington, DE (US)

( * ) Notice: Subject to any disclaimer, the term of this patent is extended or adjusted under 35 U.S.C. 154(b) by 43 days.

(21) Appl. No.: 16/310,239

(22) PCT Filed: Jun. 16, 2017

(86) PCT No.: PCT/US2017/037872
§ 371 (c)(1),
(2) Date: Dec. 14, 2018

(87) PCT Pub. No.: WO2017/218892
PCT Pub. Date: Dec. 21, 2017

(65) Prior Publication Data
US 2019/0233399 A1    Aug. 1, 2019

Related U.S. Application Data

(60) Provisional application No. 62/351,749, filed on Jun. 17, 2016.

(51) Int. Cl.
| | | |
|---|---|---|
| *C07D 403/04* | (2006.01) | |
| *C07C 309/04* | (2006.01) | |
| *C07C 309/30* | (2006.01) | |
| *A61P 35/04* | (2006.01) | |
| *A61P 35/00* | (2006.01) | |
| *A61K 31/506* | (2006.01) | |
| *A61K 45/06* | (2006.01) | |

(52) U.S. Cl.
CPC .......... *C07D 403/04* (2013.01); *A61K 31/506* (2013.01); *A61K 45/06* (2013.01); *A61P 35/00* (2018.01); *A61P 35/04* (2018.01); *C07C 309/04* (2013.01); *C07C 309/30* (2013.01); *C07B 2200/13* (2013.01)

(58) Field of Classification Search
CPC .................................................. C07D 403/04
See application file for complete search history.

(56) References Cited

U.S. PATENT DOCUMENTS

2013/0053409 A1    2/2013    Butterworth et al.

FOREIGN PATENT DOCUMENTS

| EP | 3216786 A1 | 9/2017 | |
|---|---|---|---|
| WO | 2013053409 A2 | 4/2013 | |
| WO | 2015195228 A1 | 12/2015 | |
| WO | 2016011979 A1 | 1/2016 | |
| WO | 2016029839 A1 | 3/2016 | |
| WO | 2016070816 A1 | 5/2016 | |
| WO | 2016/094821 A2 * | 6/2016 | .......... C07D 403/04 |
| WO | 2016094821 A2 | 6/2016 | |
| WO | 2016124137 A1 | 8/2016 | |
| WO | 2016202125 A1 | 12/2016 | |
| WO | 2017197062 A1 | 11/2017 | |

OTHER PUBLICATIONS

Pinedo et al. (2000).*
McMahon et al. (2000).*
Hilfiker et al., "Solid State and Polymorphism of the Drug Substance in the Context of Quality by Design and ICH Guidelines Q8-Q12" Polymorphism in the Pharmaceutical Industry: Solid Form and Drug Development, First Ed., Wiley-VCH Verlag GmbH & Co. KGaA, 2019, pp. 1-30.

* cited by examiner

*Primary Examiner* — Paul V Ward
(74) *Attorney, Agent, or Firm* — Fox Rothschild LLP

(57) ABSTRACT

Crystalline forms of N-(2-(2-(dimethylamino)ethoxy)-4-methoxy-5-((4-(1-methyl-1H-indol-3-yl)pyrimidin-2-yl)amino)phenyl)acrylamide (1) and its pharmaceutically acceptable salts and compositions thereof useful for the treatment or prevention of diseases or medical conditions mediated through mutated forms of epidermal growth factor receptor (EGFR), such as various cancers, are disclosed.

23 Claims, 17 Drawing Sheets

[C14121930-L.raw] — Peak Search Report

SCAN: 4.0/40.0056/0.01973/18.6(sec), Cu(40kV,40mA), I(max)=14805, 01/08/15 16:09

PEAK: 19-pts/Parabolic Filter, Threshold=3.0, Cutoff=0.5%, BG=3/1.0, Peak-Top=Summit NOTE: Intensity = Counts, 2T(0)=0.0(°), Wavelength to Compute d-Spacing = 1.54056A(Cu/K-alpha1)

| #  | 2-Theta | d(A)   | BG  | Height | I%    | Area   | I%    | FWHM  |
|----|---------|--------|-----|--------|-------|--------|-------|-------|
| 1  | 8.556   | 10.3262| 324 | 14481  | 100.0 | 172915 | 100.0 | 0.200 |
| 2  | 9.546   | 9.2577 | 332 | 3386   | 23.4  | 46057  | 26.6  | 0.228 |
| 3  | 9.994   | 8.8434 | 307 | 774    | 5.3   | 6510   | 3.8   | 0.141 |
| 4  | 12.190  | 7.2545 | 242 | 2449   | 16.9  | 24357  | 14.1  | 0.167 |
| 5  | 12.523  | 7.0623 | 235 | 3358   | 23.1  | 32266  | 18.6  | 0.161 |
| 6  | 15.702  | 5.6382 | 283 | 1358   | 9.4   | 22161  | 12.8  | 0.274 |
| 7  | 15.994  | 5.5367 | 304 | 2955   | 20.4  | 27132  | 15.7  | 0.154 |
| 8  | 16.744  | 5.2904 | 314 | 7057   | 48.7  | 56328  | 32.6  | 0.134 |
| 9  | 16.980  | 5.2173 | 299 | 963    | 6.6   | 14186  | 8.2   | 0.242 |
| 10 | 17.454  | 5.0767 | 296 | 323    | 2.2   | 3613   | 2.1   | 0.188 |
| 11 | 18.502  | 4.7916 | 299 | 327    | 2.3   | 1847   | 1.1   | 0.095 |
| 12 | 19.172  | 4.6255 | 285 | 879    | 6.1   | 12836  | 7.4   | 0.245 |
| 13 | 19.392  | 4.5736 | 355 | 2087   | 14.4  | 21131  | 12.2  | 0.170 |
| 14 | 19.685  | 4.5062 | 303 | 2398   | 16.6  | 23524  | 13.6  | 0.165 |
| 15 | 20.021  | 4.4312 | 331 | 3726   | 25.7  | 33980  | 19.7  | 0.153 |
| 16 | 20.238  | 4.3842 | 311 | 1561   | 10.8  | 14718  | 8.5   | 0.158 |
| 17 | 21.800  | 4.0735 | 310 | 240    | 1.7   | 2449   | 1.4   | 0.171 |
| 18 | 22.370  | 3.9685 | 322 | 209    | 1.4   | 4124   | 2.4   | 0.331 |
| 19 | 22.604  | 3.9304 | 348 | 195    | 1.3   | 4123   | 2.4   | 0.355 |
| 20 | 23.159  | 3.8374 | 368 | 4395   | 30.4  | 45148  | 26.1  | 0.172 |
| 21 | 23.473  | 3.7869 | 390 | 1926   | 13.3  | 42667  | 24.7  | 0.372 |
| 22 | 23.789  | 3.7403 | 405 | 3867   | 26.7  | 47175  | 27.3  | 0.205 |
| 23 | 24.418  | 3.6423 | 431 | 947    | 6.5   | 10871  | 6.3   | 0.193 |
| 24 | 24.894  | 3.5738 | 436 | 702    | 4.8   | 7798   | 4.5   | 0.186 |
| 25 | 25.169  | 3.5353 | 426 | 5507   | 38.0  | 53456  | 30.9  | 0.163 |
| 26 | 25.585  | 3.4788 | 431 | 1820   | 12.6  | 14185  | 8.2   | 0.131 |
| 27 | 26.349  | 3.3796 | 380 | 360    | 2.5   | 3997   | 2.3   | 0.186 |
| 28 | 26.723  | 3.3332 | 395 | 846    | 5.8   | 9181   | 5.3   | 0.182 |
| 29 | 27.161  | 3.2804 | 351 | 329    | 2.3   | 4830   | 2.8   | 0.247 |
| 30 | 27.712  | 3.2164 | 357 | 372    | 2.6   | 3726   | 2.2   | 0.168 |
| 31 | 28.464  | 3.1331 | 281 | 2992   | 20.7  | 31499  | 18.2  | 0.177 |
| 32 | 28.775  | 3.1000 | 311 | 135    | 0.9   | 1255   | 0.7   | 0.156 |
| 33 | 30.179  | 2.9589 | 224 | 193    | 1.3   | 1988   | 1.1   | 0.173 |
| 34 | 31.288  | 2.8563 | 234 | 226    | 1.6   | 2916   | 1.7   | 0.216 |
| 35 | 32.056  | 2.7898 | 224 | 1281   | 8.8   | 15483  | 9.0   | 0.203 |
| 36 | 33.237  | 2.6933 | 204 | 180    | 1.2   | 1807   | 1.0   | 0.168 |
| 37 | 35.073  | 2.5564 | 187 | 270    | 1.9   | 6356   | 3.7   | 0.395 |
| 38 | 36.471  | 2.4615 | 202 | 171    | 1.2   | 2641   | 1.5   | 0.259 |
| 39 | 36.752  | 2.4434 | 187 | 326    | 2.3   | 7658   | 4.5   | 0.404 |
| 40 | 38.766  | 2.3209 | 218 | 194    | 1.3   | 2424   | 1.4   | 0.210 |
| 41 | 39.275  | 2.2920 | 194 | 239    | 1.7   | 6048   | 3.5   | 0.424 |

Figure 1B

[scale up of mesylate-bruke-20150204.raw]  Peak Search Report

SCAN: 4.0/39.9956/0.01972/18.6(sec), Cu(40kV,40mA), I(max)=6325, 02/05/15 14:57

PEAK: 21-pts/Parabolic Filter, Threshold=3.0, Cutoff=0.5%, BG=3/1.0, Peak-Top=Summit NOTE: Intensity = Counts, 2T(0)=0.0(°), Wavelength to Compute d-Spacing = 1.54056A(Cu/K-alpha1)

| #  | 2-Theta | d(A)    | BG  | Height | I%    | Area   | I%    | FWHM  |
|----|---------|---------|-----|--------|-------|--------|-------|-------|
| 1  | 8.536   | 10.3505 | 236 | 224    | 3.8   | 2771   | 2.7   | 0.297 |
| 2  | 9.659   | 9.1489  | 226 | 336    | 5.7   | 4853   | 4.8   | 0.242 |
| 3  | 11.140  | 7.9358  | 213 | 892    | 15.2  | 12431  | 12.2  | 0.234 |
| 4  | 12.639  | 6.9981  | 272 | 1107   | 18.8  | 13835  | 13.6  | 0.210 |
| 5  | 13.329  | 6.6370  | 261 | 479    | 8.1   | 9412   | 9.3   | 0.329 |
| 6  | 13.803  | 6.4102  | 294 | 670    | 11.4  | 6765   | 6.7   | 0.169 |
| 7  | 14.729  | 6.0093  | 276 | 1609   | 27.4  | 20216  | 19.9  | 0.211 |
| 8  | 15.539  | 5.6980  | 297 | 1941   | 33.0  | 23875  | 23.5  | 0.206 |
| 9  | 16.681  | 5.3193  | 286 | 1591   | 27.1  | 19464  | 19.2  | 0.205 |
| 10 | 17.904  | 4.9500  | 295 | 2530   | 43.0  | 33194  | 32.7  | 0.220 |
| 11 | 18.229  | 4.8650  | 307 | 458    | 7.8   | 12657  | 12.5  | 0.463 |
| 12 | 19.285  | 4.5987  | 329 | 2067   | 35.1  | 31102  | 30.6  | 0.252 |
| 13 | 19.898  | 4.4584  | 353 | 640    | 10.9  | 11071  | 10.9  | 0.290 |
| 14 | 20.943  | 4.2382  | 355 | 1295   | 22.0  | 16215  | 16.0  | 0.210 |
| 15 | 22.127  | 4.0141  | 444 | 5881   | 100.0 | 101542 | 100.0 | 0.289 |
| 16 | 23.171  | 3.8356  | 402 | 1935   | 32.9  | 37068  | 36.5  | 0.321 |
| 17 | 24.314  | 3.6577  | 353 | 875    | 14.9  | 11965  | 11.8  | 0.229 |
| 18 | 25.164  | 3.5361  | 463 | 1781   | 30.3  | 33502  | 33.0  | 0.315 |
| 19 | 25.794  | 3.4511  | 420 | 1028   | 17.5  | 30779  | 30.3  | 0.502 |
| 20 | 26.229  | 3.3949  | 561 | 557    | 9.5   | 4436   | 4.4   | 0.134 |
| 21 | 26.781  | 3.3261  | 381 | 290    | 4.9   | 3450   | 3.4   | 0.199 |
| 22 | 27.373  | 3.2555  | 357 | 969    | 16.5  | 19563  | 19.3  | 0.338 |
| 23 | 28.832  | 3.0940  | 262 | 124    | 2.1   | 3438   | 3.4   | 0.465 |
| 24 | 29.324  | 3.0432  | 295 | 280    | 4.8   | 7546   | 7.4   | 0.452 |
| 25 | 30.055  | 2.9708  | 290 | 401    | 6.8   | 6753   | 6.7   | 0.282 |
| 26 | 30.705  | 2.9093  | 307 | 77     | 1.3   | 727    | 0.7   | 0.158 |
| 27 | 31.160  | 2.8680  | 292 | 148    | 2.5   | 5510   | 5.4   | 0.624 |
| 28 | 31.535  | 2.8347  | 247 | 292    | 5.0   | 11903  | 11.7  | 0.683 |
| 29 | 32.009  | 2.7938  | 296 | 173    | 2.9   | 2323   | 2.3   | 0.225 |
| 30 | 32.835  | 2.7253  | 228 | 115    | 2.0   | 1626   | 1.6   | 0.266 |
| 31 | 33.644  | 2.6616  | 233 | 408    | 6.9   | 9725   | 9.6   | 0.400 |
| 32 | 35.777  | 2.5077  | 203 | 63     | 1.1   | 840    | 0.8   | 0.224 |
| 33 | 36.682  | 2.4479  | 215 | 183    | 3.1   | 5249   | 5.2   | 0.481 |
| 34 | 37.178  | 2.4165  | 223 | 101    | 1.7   | 3590   | 3.5   | 0.596 |
| 35 | 38.417  | 2.3412  | 244 | 456    | 7.8   | 12133  | 11.9  | 0.446 |
| 36 | 38.811  | 2.3183  | 233 | 264    | 4.5   | 9326   | 9.2   | 0.592 |

Figure 5B

| # | 2-Theta | d(A) | BG | Height | I% | Area | I% | FWHM |
|---|---------|------|-----|--------|------|-------|-------|-------|
| 1 | 6.406 | 13.7854 | 335 | 212 | 45.5 | 3826 | 31.0 | 0.303 |
| 2 | 9.702 | 9.1083 | 274 | 333 | 71.5 | 6396 | 51.8 | 0.322 |
| 3 | 12.779 | 6.9214 | 346 | 466 | 100.0 | 9802 | 79.4 | 0.353 |
| 4 | 15.700 | 5.6397 | 387 | 268 | 57.5 | 4999 | 40.5 | 0.313 |
| 5 | 18.204 | 4.8692 | 642 | 417 | 89.5 | 9577 | 77.5 | 0.385 |
| 6 | 20.276 | 4.3762 | 696 | 216 | 46.4 | 7187 | 58.2 | 0.558 |
| 7 | 22.385 | 3.9683 | 524 | 94 | 20.2 | 4315 | 34.9 | 0.770 |
| 8 | 22.801 | 3.8969 | 524 | 89 | 19.1 | 3695 | 29.9 | 0.696 |
| 9 | 25.110 | 3.5436 | 510 | 311 | 66.7 | 11187 | 90.6 | 0.603 |
| 10 | 25.623 | 3.4738 | 499 | 289 | 62.0 | 12350 | 100.0 | 0.717 |
| 11 | 26.847 | 3.3181 | 469 | 181 | 38.8 | 4345 | 35.2 | 0.403 |
| 12 | 28.190 | 3.1630 | 392 | 72 | 15.5 | 1500 | 12.1 | 0.349 |

[scale up of solid from API with HCl.raw]  Peak Search Report

SCAN: 4.0/40.0056/0.01973/18.6(sec), Cu(40kV,40mA), I(max)=3856, 01/15/15 16:54

PEAK: 19-pts/Parabolic Filter, Threshold=3.0, Cutoff=0.5%, BG=3/1.0, Peak-Top=Summit NOTE: Intensity = Counts, 2T(0)=0.0(°), Wavelength to Compute d-Spacing = 1.54056A(Cu/K-alpha1)

| # | 2-Theta | d(A) | BG | Height | I% | Area | I% | FWHM |
|---|---------|------|----|--------|----|------|----|------|
| 1 | 6.366 | 13.8246 | 303 | 423 | 11.8 | 3647 | 8.8 | 0.145 |
| 2 | 8.457 | 10.4465 | 228 | 3360 | 93.4 | 31375 | 75.8 | 0.157 |
| 3 | 9.030 | 9.7859 | 230 | 681 | 18.9 | 6962 | 16.7 | 0.170 |
| 4 | 10.588 | 8.3485 | 226 | 221 | 6.1 | 1765 | 4.3 | 0.134 |
| 5 | 11.199 | 7.8940 | 201 | 2630 | 73.1 | 23899 | 57.8 | 0.152 |
| 6 | 11.735 | 7.5351 | 204 | 177 | 4.9 | 2036 | 4.9 | 0.193 |
| 7 | 12.483 | 7.0651 | 193 | 360 | 10.0 | 4593 | 11.1 | 0.214 |
| 8 | 12.741 | 6.9424 | 188 | 870 | 24.2 | 8293 | 20.0 | 0.160 |
| 9 | 14.456 | 6.1222 | 176 | 172 | 4.8 | 2391 | 5.8 | 0.233 |
| 10 | 16.132 | 5.4896 | 193 | 1235 | 34.3 | 10874 | 26.3 | 0.148 |
| 11 | 16.902 | 5.2414 | 214 | 197 | 5.5 | 2095 | 5.1 | 0.178 |
| 12 | 17.258 | 5.1339 | 224 | 1325 | 36.8 | 13998 | 33.8 | 0.177 |
| 13 | 18.066 | 4.9062 | 238 | 1957 | 54.4 | 21701 | 52.5 | 0.186 |
| 14 | 18.699 | 4.7415 | 241 | 688 | 19.1 | 6248 | 15.1 | 0.153 |
| 15 | 19.231 | 4.6114 | 238 | 274 | 7.6 | 3403 | 8.2 | 0.298 |
| 16 | 19.785 | 4.4881 | 239 | 499 | 13.9 | 5116 | 12.4 | 0.172 |
| 17 | 20.591 | 4.3098 | 266 | 1131 | 31.4 | 10969 | 26.5 | 0.163 |
| 18 | 20.929 | 4.2411 | 282 | 291 | 8.1 | 3125 | 7.6 | 0.180 |
| 19 | 21.186 | 4.1902 | 294 | 299 | 8.3 | 2578 | 6.2 | 0.145 |
| 20 | 21.775 | 4.0782 | 297 | 1086 | 30.2 | 16750 | 40.5 | 0.259 |
| 21 | 22.426 | 3.9612 | 289 | 3458 | 96.1 | 35349 | 85.4 | 0.171 |
| 22 | 23.570 | 3.7714 | 258 | 3598 | 100.0 | 41371 | 100.0 | 0.193 |
| 23 | 24.280 | 3.6627 | 265 | 79 | 2.2 | 821 | 2.0 | 0.174 |
| 24 | 25.069 | 3.5492 | 249 | 411 | 11.4 | 4469 | 10.8 | 0.182 |
| 25 | 25.426 | 3.5002 | 262 | 834 | 23.2 | 13421 | 32.4 | 0.279 |
| 26 | 26.355 | 3.3916 | 259 | 1474 | 41.0 | 14598 | 35.3 | 0.166 |
| 27 | 26.896 | 3.3133 | 247 | 578 | 16.1 | 8378 | 20.3 | 0.243 |
| 28 | 27.616 | 3.2274 | 220 | 253 | 7.0 | 7856 | 19.0 | 0.521 |
| 29 | 28.030 | 3.1806 | 217 | 280 | 7.8 | 7082 | 17.1 | 0.424 |
| 30 | 28.503 | 3.1289 | 199 | 109 | 3.0 | 1509 | 3.6 | 0.232 |
| 31 | 29.252 | 3.0505 | 184 | 382 | 10.6 | 5150 | 12.4 | 0.226 |
| 32 | 29.766 | 2.9988 | 169 | 110 | 3.1 | 1015 | 2.5 | 0.155 |
| 33 | 30.261 | 2.9511 | 164 | 157 | 4.4 | 2917 | 7.1 | 0.312 |
| 34 | 30.866 | 2.8944 | 153 | 72 | 2.0 | 961 | 2.3 | 0.224 |
| 35 | 31.659 | 2.8238 | 158 | 62 | 1.7 | 1845 | 4.5 | 0.499 |
| 36 | 31.977 | 2.7965 | 172 | 97 | 2.7 | 1857 | 4.6 | 0.321 |
| 37 | 32.470 | 2.7551 | 167 | 134 | 3.7 | 3686 | 8.9 | 0.461 |
| 38 | 32.804 | 2.7279 | 179 | 201 | 5.6 | 3715 | 9.0 | 0.310 |
| 39 | 33.278 | 2.6901 | 170 | 90 | 2.5 | 890 | 2.2 | 0.166 |
| 40 | 33.652 | 2.6610 | 157 | 184 | 5.1 | 4634 | 11.7 | 0.441 |
| 41 | 34.087 | 2.6296 | 145 | 103 | 2.9 | 1818 | 4.4 | 0.296 |
| 42 | 35.014 | 2.5605 | 131 | 95 | 2.6 | 2455 | 5.9 | 0.433 |
| 43 | 35.567 | 2.5220 | 129 | 55 | 1.5 | 895 | 2.2 | 0.273 |
| 44 | 36.217 | 2.4782 | 124 | 54 | 1.5 | 2411 | 5.8 | 0.749 |
| 45 | 36.533 | 2.4575 | 120 | 72 | 2.0 | 2682 | 6.5 | 0.625 |
| 46 | 36.829 | 2.4385 | 117 | 87 | 2.4 | 2674 | 6.5 | 0.515 |
| 47 | 37.895 | 2.3723 | 106 | 83 | 2.3 | 1679 | 4.1 | 0.339 |

Figure 14B

[scale up of solid from API with H2SO4.raw]    Peak Search Report

SCAN: 4.0/40.0056/0.01973/16.6(sec), Cu(40kV,40mA), I(max)=4440, 01/15/15 16:54

PEAK: 21-pts/Parabolic Filter, Threshold=3.0, Cutoff=0.5%, BG=3/1.0, Peak-Top=Summit NOTE: Intensity = Counts, 2T(0)=0.0(°), Wavelength to Compute d-Spacing = 1.54056A(Cu/K-alpha1)

| #  | 2-Theta | d(A)    | BG  | Height | I%    | Area  | I%    | FWHM  |
|----|---------|---------|-----|--------|-------|-------|-------|-------|
| 1  | 5.558   | 15.8861 | 413 | 4027   | 100.0 | 70968 | 100.0 | 0.296 |
| 2  | 5.912   | 14.9358 | 401 | 834    | 20.7  | 18347 | 25.9  | 0.369 |
| 3  | 7.255   | 12.1748 | 289 | 537    | 13.3  | 5849  | 8.2   | 0.183 |
| 4  | 11.024  | 8.0190  | 241 | 1763   | 43.8  | 34437 | 48.5  | 0.328 |
| 5  | 11.932  | 7.4108  | 412 | 320    | 7.9   | 5335  | 7.5   | 0.280 |
| 6  | 13.233  | 6.6853  | 326 | 108    | 2.7   | 2158  | 3.0   | 0.335 |
| 7  | 13.589  | 6.5106  | 318 | 353    | 8.8   | 7006  | 9.9   | 0.333 |
| 8  | 14.318  | 6.1808  | 311 | 1015   | 25.2  | 14553 | 20.5  | 0.240 |
| 9  | 15.462  | 5.7262  | 300 | 111    | 2.8   | 1636  | 2.3   | 0.247 |
| 10 | 15.759  | 5.6188  | 305 | 316    | 7.8   | 5664  | 8.0   | 0.301 |
| 11 | 17.119  | 5.1754  | 434 | 254    | 6.3   | 2110  | 3.0   | 0.139 |
| 12 | 17.515  | 5.0592  | 372 | 392    | 9.7   | 7707  | 10.9  | 0.330 |
| 13 | 18.126  | 4.8901  | 419 | 948    | 23.5  | 16206 | 22.8  | 0.287 |
| 14 | 19.032  | 4.6591  | 527 | 429    | 10.7  | 4640  | 6.5   | 0.181 |
| 15 | 19.606  | 4.5241  | 401 | 1821   | 45.2  | 39353 | 55.5  | 0.362 |
| 16 | 19.862  | 4.4664  | 448 | 1205   | 29.9  | 38415 | 54.1  | 0.535 |
| 17 | 20.633  | 4.3012  | 419 | 166    | 4.1   | 2835  | 4.0   | 0.286 |
| 18 | 21.302  | 4.1675  | 451 | 226    | 5.6   | 4627  | 6.5   | 0.343 |
| 19 | 21.736  | 4.0853  | 459 | 104    | 2.6   | 1389  | 2.0   | 0.224 |
| 20 | 22.171  | 4.0062  | 433 | 673    | 16.7  | 13762 | 19.4  | 0.343 |
| 21 | 22.621  | 3.8935  | 410 | 139    | 3.5   | 1314  | 1.9   | 0.159 |
| 22 | 23.374  | 3.8026  | 429 | 90     | 2.2   | 861   | 1.2   | 0.164 |
| 23 | 23.947  | 3.7130  | 601 | 370    | 9.2   | 3861  | 5.4   | 0.175 |
| 24 | 24.361  | 3.6508  | 490 | 344    | 8.5   | 11257 | 15.9  | 0.549 |
| 25 | 24.912  | 3.5712  | 571 | 1261   | 31.3  | 28913 | 40.7  | 0.385 |
| 26 | 25.742  | 3.4579  | 490 | 150    | 3.7   | 1840  | 2.6   | 0.206 |
| 27 | 26.295  | 3.3865  | 459 | 861    | 21.4  | 12452 | 17.5  | 0.243 |
| 28 | 27.616  | 3.2274  | 368 | 72     | 1.8   | 1139  | 1.6   | 0.265 |
| 29 | 28.839  | 3.0932  | 307 | 611    | 15.2  | 11559 | 16.3  | 0.317 |
| 30 | 29.628  | 3.0126  | 283 | 114    | 2.8   | 1644  | 2.3   | 0.242 |
| 31 | 31.206  | 2.8638  | 200 | 197    | 4.9   | 4986  | 7.0   | 0.424 |
| 32 | 33.140  | 2.7009  | 187 | 171    | 4.2   | 2845  | 4.0   | 0.279 |
| 33 | 34.027  | 2.6326  | 197 | 118    | 2.9   | 2046  | 2.9   | 0.291 |

Figure 16B

| # | 2-Theta | d(A) | BG | Height | I% | Area | I% | FWHM |
|---|---------|---------|-----|--------|-------|-------|-------|-------|
| 1 | 6.820 | 12.9494 | 308 | 1725 | 100.0 | 27009 | 100.0 | 0.263 |
| 2 | 7.335 | 12.0424 | 287 | 859 | 49.8 | 14730 | 54.5 | 0.288 |
| 3 | 10.334 | 8.5531 | 204 | 240 | 13.9 | 3313 | 12.3 | 0.231 |
| 4 | 11.319 | 7.8112 | 216 | 502 | 29.1 | 9106 | 33.7 | 0.304 |
| 5 | 13.094 | 6.7555 | 209 | 500 | 29.0 | 8917 | 33.0 | 0.299 |
| 6 | 14.652 | 6.0405 | 226 | 104 | 6.0 | 1264 | 4.7 | 0.204 |
| 7 | 15.325 | 5.7769 | 251 | 105 | 6.1 | 4182 | 15.5 | 0.668 |
| 8 | 15.661 | 5.6539 | 238 | 274 | 15.9 | 8375 | 31.0 | 0.513 |
| 9 | 16.430 | 5.3909 | 265 | 114 | 6.6 | 1224 | 4.5 | 0.180 |
| 10 | 18.185 | 4.8743 | 268 | 326 | 18.9 | 10647 | 39.4 | 0.546 |
| 11 | 18.698 | 4.7417 | 291 | 82 | 4.8 | 2966 | 11.0 | 0.607 |
| 12 | 19.821 | 4.4754 | 285 | 81 | 4.7 | 1017 | 3.8 | 0.211 |
| 13 | 20.553 | 4.3178 | 248 | 556 | 32.2 | 13365 | 49.5 | 0.403 |
| 14 | 22.664 | 3.9202 | 265 | 345 | 20.0 | 12716 | 47.1 | 0.618 |
| 15 | 23.295 | 3.8153 | 293 | 223 | 12.9 | 5979 | 22.1 | 0.450 |
| 16 | 24.616 | 3.6135 | 262 | 187 | 10.8 | 3949 | 14.6 | 0.354 |
| 17 | 25.309 | 3.5161 | 257 | 74 | 4.3 | 1542 | 5.7 | 0.349 |
| 18 | 27.044 | 3.2944 | 205 | 336 | 19.5 | 10204 | 37.8 | 0.509 |
| 19 | 29.746 | 3.0009 | 194 | 207 | 12.0 | 5846 | 21.6 | 0.474 |

[scale up of potential citrate in Acetone-after dry.raw]     Peak Search Report

SCAN: 4.0/40,0.0056/0.01973/18.6(sec), Cu(40kV,40mA), I(max)=1775, 01/21/15 10:13

PEAK: 27-pts/Parabolic Filter, Threshold=3.0, Cutoff=0.5%, BG=3/1.0, Peak-Top=Summit NOTE: Intensity = Counts, 2T(0)=0.0(°), Wavelength to Compute d-Spacing = 1.54056A(Cu/K-alpha1)

| # | 2-Theta | d(A) | BG | Height | I% | Area | I% | FWHM |
|---|---------|------|----|--------|----|------|----|------|
| 1 | 5.953 | 14.8333 | 388 | 1296 | 87.8 | 26787 | 70.0 | 0.347 |
| 2 | 8.024 | 11.0091 | 285 | 1324 | 89.7 | 24833 | 64.9 | 0.315 |
| 3 | 11.831 | 7.4737 | 285 | 150 | 10.2 | 2041 | 5.3 | 0.228 |
| 4 | 12.563 | 7.0402 | 280 | 953 | 64.6 | 18796 | 49.1 | 0.331 |
| 5 | 13.233 | 6.6850 | 299 | 1476 | 100.0 | 38278 | 100.0 | 0.435 |
| 6 | 14.830 | 5.9687 | 285 | 244 | 16.5 | 6266 | 16.4 | 0.431 |
| 7 | 15.165 | 5.8397 | 291 | 196 | 13.3 | 5273 | 13.8 | 0.451 |
| 8 | 16.032 | 5.5235 | 362 | 339 | 23.0 | 5021 | 13.1 | 0.248 |
| 9 | 16.609 | 5.3330 | 341 | 342 | 23.2 | 12629 | 33.0 | 0.619 |
| 10 | 17.041 | 5.1988 | 383 | 588 | 39.8 | 14900 | 38.9 | 0.426 |
| 11 | 17.772 | 4.9868 | 495 | 255 | 17.3 | 2828 | 7.4 | 0.186 |
| 12 | 18.576 | 4.7720 | 417 | 322 | 21.8 | 17460 | 45.7 | 0.910 |
| 13 | 19.053 | 4.6542 | 452 | 642 | 43.5 | 15169 | 39.6 | 0.398 |
| 14 | 19.861 | 4.4665 | 448 | 272 | 18.4 | 8280 | 21.6 | 0.510 |
| 15 | 20.296 | 4.3717 | 356 | 607 | 41.1 | 24603 | 64.3 | 0.660 |
| 16 | 22.171 | 4.0062 | 302 | 423 | 28.7 | 8023 | 21.0 | 0.318 |
| 17 | 24.734 | 3.5965 | 529 | 497 | 33.7 | 10569 | 27.6 | 0.357 |
| 18 | 25.132 | 3.5405 | 610 | 163 | 11.0 | 2552 | 6.7 | 0.263 |
| 19 | 26.626 | 3.4733 | 734 | 192 | 13.0 | 1815 | 4.7 | 0.159 |
| 20 | 26.492 | 3.3618 | 627 | 803 | 54.4 | 29483 | 77.0 | 0.616 |
| 21 | 28.244 | 3.1570 | 392 | 77 | 5.2 | 328 | 0.9 | 0.071 |
| 22 | 29.565 | 3.0189 | 285 | 76 | 5.1 | 2821 | 7.4 | 0.622 |
| 23 | 30.221 | 2.9549 | 268 | 135 | 9.1 | 3999 | 10.4 | 0.497 |
| 24 | 31.641 | 2.8254 | 242 | 94 | 6.4 | 2812 | 7.3 | 0.502 |
| 25 | 32.147 | 2.7821 | 246 | 57 | 3.9 | 1835 | 4.8 | 0.481 |
| 26 | 33.561 | 2.6688 | 209 | 98 | 6.6 | 2422 | 6.3 | 0.414 |
| 27 | 34.756 | 2.5790 | 198 | 127 | 8.6 | 4666 | 12.2 | 0.616 |
| 28 | 35.073 | 2.5564 | 193 | 144 | 9.8 | 4680 | 12.2 | 0.546 |
| 29 | 37.001 | 2.4275 | 194 | 65 | 4.4 | 1225 | 3.2 | 0.316 |
| 30 | 38.709 | 2.3242 | 196 | 56 | 3.8 | 1170 | 3.1 | 0.350 |
| 31 | 39.592 | 2.2744 | 202 | 53 | 3.6 | 834 | 2.2 | 0.264 |

Figure 21B

PHARMACEUTICAL SALTS N-(2-(2-(DIMETHYLAMINO)ETHOXY)-4-METHOXY-5-((4-(1-METHYL-1H-INDOL-3-YL)PYRIMIDIN-2-YL)AMINO)PHENYL) ACRYLAMIDE AND CRYSTALLINE FORMS THEREOF

CROSS REFERENCE TO RELATED APPLICATIONS

This application is a U.S. national phase application of International Application No. PCT/US2017/037872, filed on Jun. 16, 2017, which in turn claims priority under 35 U.S.C. § 119(e) to U.S. Provisional Application No. 62/351,749, filed on Jun. 17, 2016, both of which are incorporated herein by reference in their entirety.

FIELD OF THE INVENTION

The present invention relates to crystalline forms of N-(2-(2-(dimethylamino)ethoxy)-4-methoxy-5-((4-(1-methyl-1H-indol-3-yl)pyrimidin-2-yl)amino)phenyl)acrylamide (see below, compound 1) and its pharmaceutically acceptable salts and compositions thereof useful for the treatment or prevention of diseases or medical conditions mediated through mutated forms of epidermal growth factor receptor (EGFR), such as various cancers.

BACKGROUND OF THE INVENTION

The epidermal growth factor receptor (EGFR, Her1, ErbB1) is a principal member of the ErbB family of four structurally-related cell surface receptors with the other members being Her2 (Neu, ErbB2), Her3 (ErbB3) and Her4 (ErbB4). EGFR exerts its primary cellular functions through its intrinsic catalytic tyrosine protein kinase activity. The receptor is activated by binding with growth factor ligands, such as epidermal growth factor (EGF) and transforming growth factor-alpha (TGF-α), which transform the catalytically inactive EGFR monomer into catalytically active homo- and hetero-dimers. These catalytically active dimers then initiate intracellular tyrosine kinase activity, which leads to the autophosphorylation of specific EGFR tyrosine residues and elicits the downstream activation of signaling proteins. Subsequently, the signaling proteins initiate multiple signal transduction cascades (MAPK, Akt and JNK), which ultimately mediate the essential biological processes of cell growth, proliferation, motility and survival.

EGFR is found at abnormally high levels on the surface of many types of cancer cells and increased levels of EGFR have been associated with advanced disease, cancer spread and poor clinical prognosis. Mutations in EGFR can lead to receptor overexpression, perpetual activation or sustained hyperactivity and result in uncontrolled cell growth, i.e. cancer. Consequently, EGFR mutations have been identified in several types of malignant tumors, including metastatic lung, head and neck, colorectal and pancreatic cancers. In lung cancer, mutations mainly occur in exons 18 to 21, which encode the adenosine triphosphate (ATP)-binding pocket of the kinase domain. The most clinically relevant drug-sensitive EGFR mutations are deletions in exon 19 that eliminate a common amino acid motif (LREA) and point mutations in exon 21, which lead to a substitution of arginine for leucine at position 858 (L858R). Together, these two mutations account for nearly 85% of the EGFR mutations observed in lung cancer. Both mutations have perpetual tyrosine kinase activity and as a result they are oncogenic.

In at least 50% of patients who are initially responsive to current therapy, disease progression is associated with the development of a secondary mutation, T790M in exon 20 of EGFR (referred to as the gatekeeper mutation).

Compound 1 effectively inhibits the kinase domain of the T790M double mutant and therefore overcomes the resistance observed with the currently used therapy of reversible inhibitors. See WO2016/092841 and International Application No. PCT/US17/32066, both of which are herein incorporated by reference in their entireties. However, to make compound 1 a viable therapeutic agent for treatment of diseases associated with T790M double mutation, there remains a need to find a suitable salt and/or crystalline form that would provide desired physical and mechanical properties, among others, for formulation. Because crystallinity and crystalline forms of a drug substance and their physical and mechanical properties, such as solubility, melting point, hardness, and compressibility, are in general unpredictable, so are their effects on the properties of a corresponding drug product, such as dissolution rate and bioavailability, the present invention sought to identify such a suitable salt and/or crystalline form of compound 1.

SUMMARY OF THE INVENTION

The present invention provides crystalline forms of compound 1 and its various pharmaceutical salts. In one aspect, the present invention provides a crystalline form of compound 1 (free base):

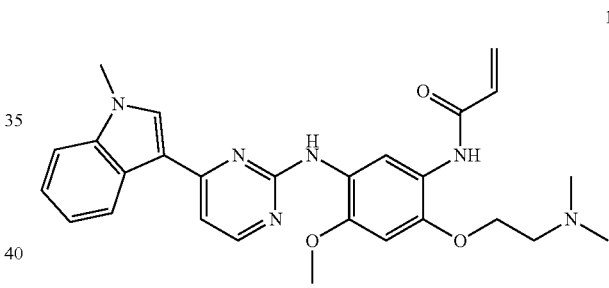

In one aspect, the present invention provides a crystalline form of the compound of formula 1, namely N-(2-(2-(dimethylamino)ethoxy)-4-methoxy-5-((4-(1-methyl-1H-indol-3-yl)pyrimidin-2-yl)amino)phenyl)acrylamide (free base), having an X-ray powder diffraction pattern comprising the following 2θ values measured using CuKα radiation: 8.5°±0.2°, 16.7°±0.2°, and 25.2°±0.2°.

In another aspect, the present invention provides a crystalline form of N-(2-(2-(dimethylamino)ethoxy)-4-methoxy-5-((4-(1-methyl-1H-indol-3-yl)pyrimidin-2-yl)amino)phenyl)acrylamide methanesulfonate salt (formula 2) having a molar ratio of about 1:1 between methanesulfonic acid and free base.

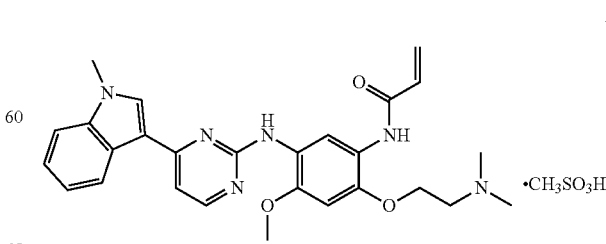

In another aspect, the present invention provides a crystalline form of N-(2-(2-(dimethylamino)ethoxy)-4- methoxy-5-((4-(1-methyl-1H-indol-3-yl)pyrimidin-2-yl) amino)phenyl)acrylamide hydrochloride salt (formula 3) having a molar ratio of about 1:1 between hydrochloride acid and free base.

3

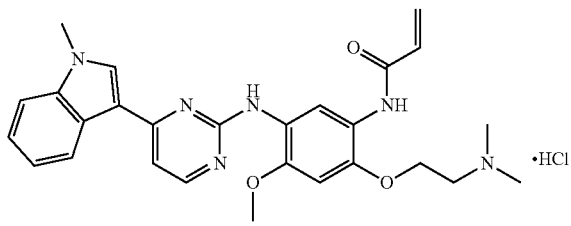

In another aspect, the present invention provides a crystalline form of N-(2-(2-(dimethylamino)ethoxy)-4-methoxy-5-((4-(1-methyl-1H-indol-3-yl)pyrimidin-2-yl) amino)phenyl)acrylamide sulfate salt (formula 4) having a molar ratio of about 1:1 between sulfuric acid and free base.

4

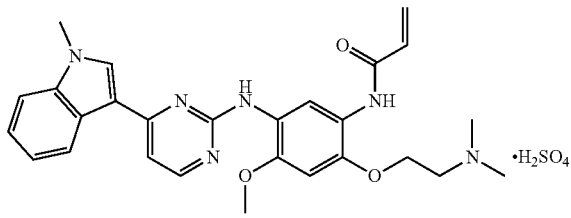

In another aspect, the present invention provides a crystalline form of N-(2-(2-(dimethylamino)ethoxy)-4-methoxy-5-((4-(1-methyl-1H-indol-3-yl)pyrimidin-2-yl) amino)phenyl)acrylamide p-toluenesulfonate (p-tosylate) salt (formula 5) having a molar ratio of about 1:1 between p-toluenesulfonic acid and free base.

5

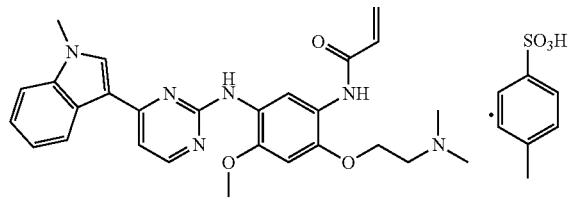

In another aspect, the present invention provides a crystalline form of N-(2-(2-(dimethylamino)ethoxy)-4-methoxy-5-((4-(1-methyl-1H-indol-3-yl)pyrimidin-2-yl) amino)phenyl)acrylamide citrate salt (formula 6) having a molar ratio of about 1:1 between citric acid and free base.

6

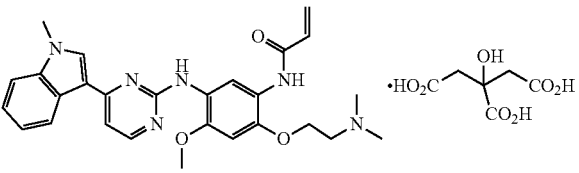

In another aspect, the present invention provides a pharmaceutical composition comprising a crystalline form according to any of embodiments disclosed here, or a combination thereof, and a pharmaceutically acceptable carrier, adjuvant, diluent, and/or vehicle.

In another aspect, the present invention provides a method of treating a disease or disorder associated with an EGFR activity, comprising administration of a therapeutically effective amount of a crystalline form according to any one of the embodiments disclosed herein, or a combination thereof, or a pharmaceutical composition thereof, to a patient in need of treatment.

In another aspect, the present invention provides a method of inhibiting a mutant of EGFR in a subject, comprising contacting a biological sample of said subject with a crystalline forms of compounds according to any embodiments disclosed herein, or a combination thereof, or a pharmaceutical composition thereof.

In another aspect, the present invention provides use of a crystalline form according to any embodiments disclosed herein, or a combination thereof, in the manufacture of a medicament for treatment of a disease or disorder associated with an EGFR activity.

In another aspect, the present invention provides processes of preparing a crystalline form according to any embodiments disclosed herein as substantially described and shown.

Other aspects or advantages of the present invention will be better appreciated in view of the detailed description and claims.

BRIEF DESCRIPTION OF THE DRAWINGS

FIGS. 1A and 1B illustrate (FIG. 1A) XRPD pattern of compound 1 (free base); and (FIG. 1B) XRPD data of pattern of compound 1 (free base).

FIGS. 5A and 5B illustrate (FIG. 5A) XRPD pattern of compound 2 (Form 2A); and (FIG. 5B) XRPD data of compound 2 (Form 2A).

(FIG. 9B) XRPD data of compound 2 (Form 2B).

FIGS. 14A and 14B illustrate (FIG. 14A) Overlay of compound 3 XRPD patterns before and after dynamic vapor sorption (DVS). (FIG. 14B) XRPD data of compound 3.

FIGS. 16A and 16B illustrate (16A) Overlay of XRPD patterns for compound 4 before (bottom) and after (top) DVS. (16B) XRPD data of compound 4 before DVS.

(FIG. 18B) XRPD data of compound 5 before DVS.

FIGS. 21A and 21B illustrate (FIG. 21A) XRPD pattern for compound 6; and (FIG. 21B) XRPD data of compound 6.

DETAILED DESCRIPTION OF THE INVENTION

In one aspect, the present invention provides a crystalline form of the compound of formula 1, namely N-(2-(2-(dimethylamino)ethoxy)-4-methoxy-5-((4-(1-methyl-1H-indol-3-yl)pyrimidin-2-yl)amino)phenyl)acrylamide (free base), having an X-ray powder diffraction pattern comprising the following 2θ values measured using CuKα radiation: 8.5°±0.2°, 16.7°±0.2°, and 25.2°±0.2°.

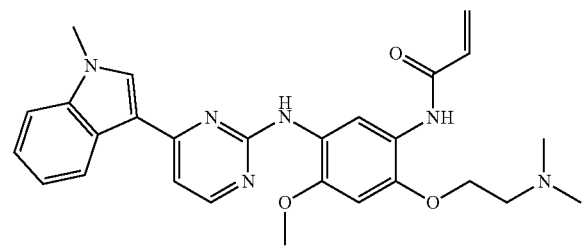

In one embodiment, the X-ray powder diffraction pattern further comprises any two or more of the following 2θ values measured using CuKα radiation: 9.5°±0.2°, 12.2°±0.2°, 12.5°±0.2°, 15.7°±0.2°, 16.0°±0.2°, 19.4°±0.2°, 19.7°±0.2°, 20.0°±0.2°, 23.2°±0.2°, 24.4°±0.2°, and 28.5°±0.2°. In one embodiment, the X-ray powder diffraction pattern comprises all of these 2θ values along 8.5°±0.2°, 16.7°±0.2°, and 25.2°±0.2°.

In another embodiment, the crystalline form of compound 1 has a melting point with an onset temperature at about 169.6° C. and/or a peak temperature at about 171.7° C. as measured by differential scanning calorimetry.

Figure 1A:
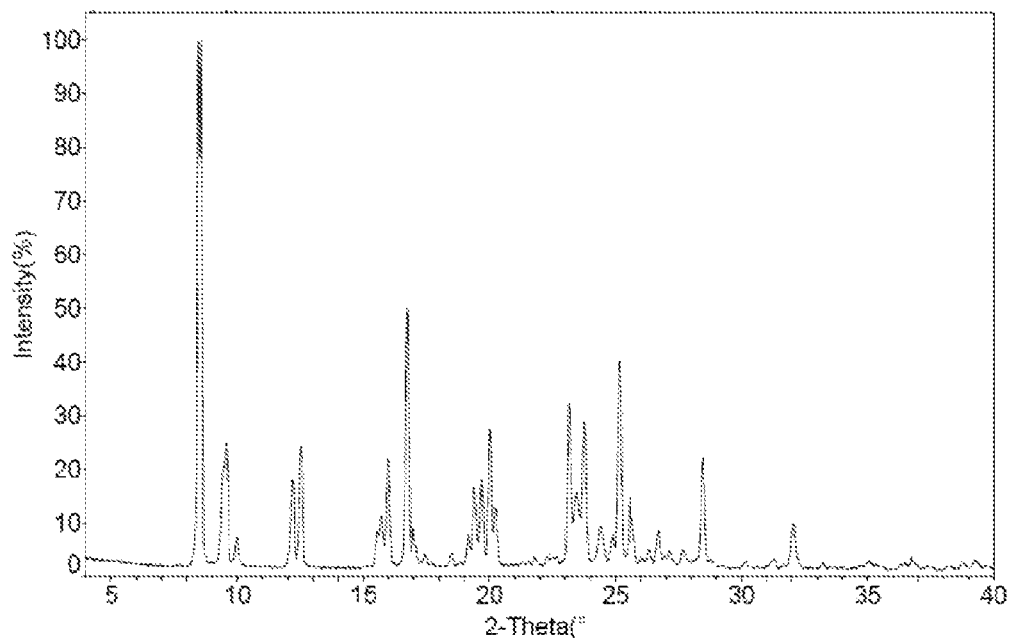

In another embodiment, the crystalline form of compound 1 has an X-ray powder diffraction pattern substantially as depicted in FIG. 1.

Figure 3:
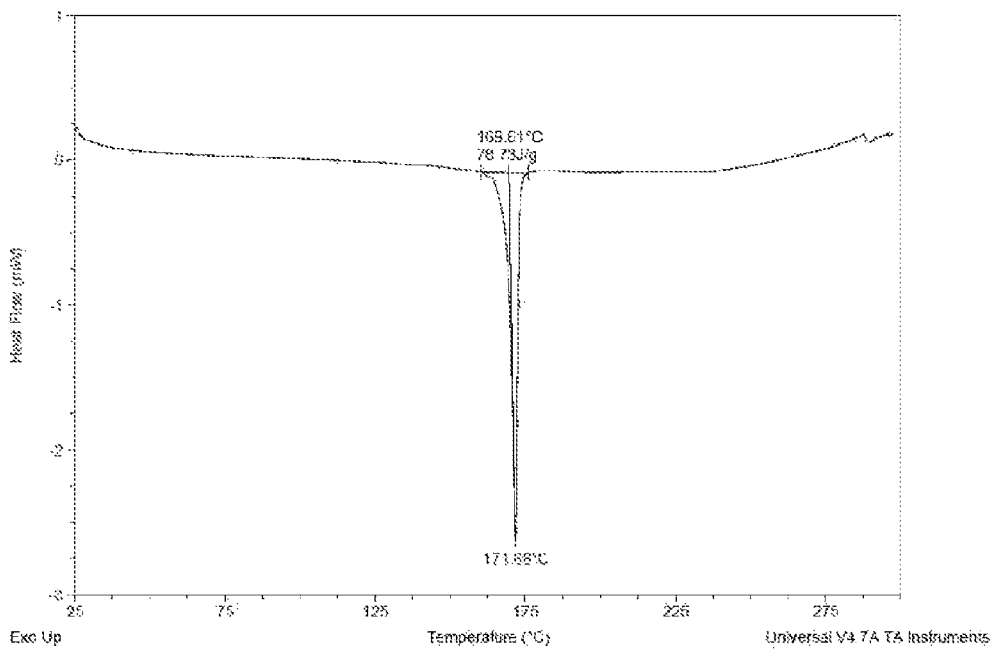
FIG. 3 illustrates DSC thermogram of compound 1 (free base).

In another embodiment, the crystalline form of compound 1 has a differential scanning calorimetric thermogram substantially as depicted in FIG. 3.

Figure 4:
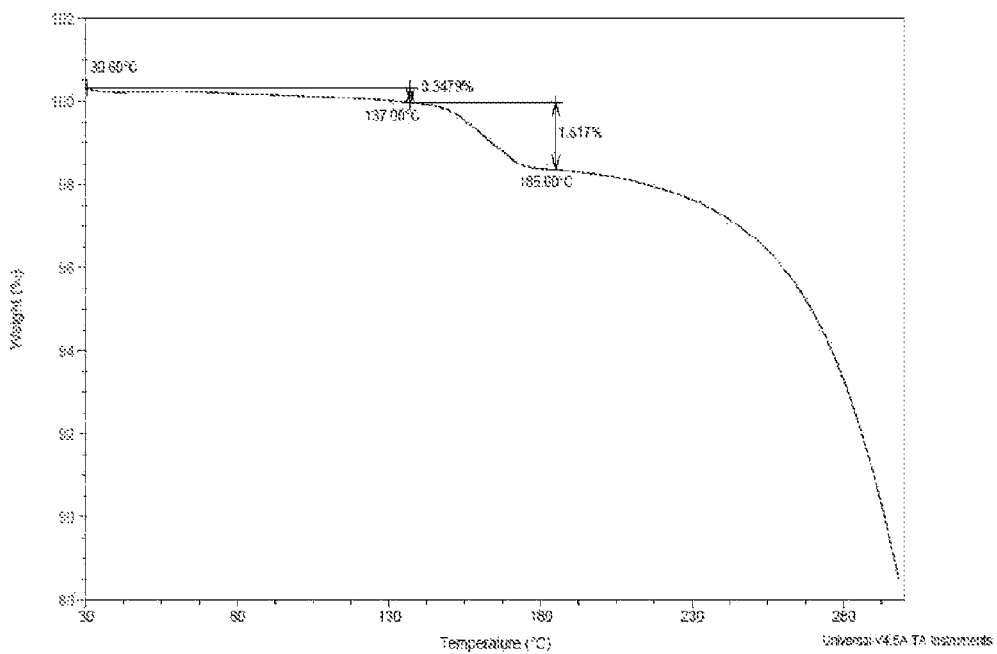
FIG. 4 illustrates TGA Thermogram of compound 1 (free base).

In another embodiment, the crystalline form of compound 1 has a thermal gravimetric analysis thermogram substantially as depicted in FIG. 4.

In another aspect, the present invention provides a crystalline form of N-(2-(2-(dimethylamino)ethoxy)-4-methoxy-5-((4-(1-methyl-1H-indo-3-yl)pyrimidin-2-yl)amino)phenyl)acrylamide methanesulfonate salt (formula 2) having a molar ratio of about 1:1 between methanesulfonic acid and free base.

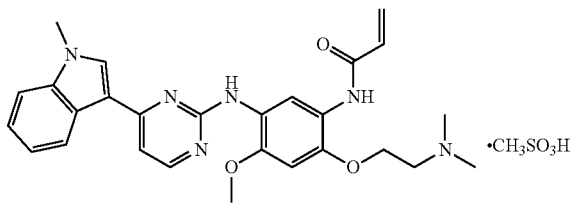

In one embodiment, the crystalline form of compound 2, designated as crystalline Form 2A, has an X-ray powder diffraction pattern comprising any three or more of the following 2θ values measured using CuKα radiation: 12.6°±0.2°, 15.5°±0.2°, 17.9°±0.2°, 22.1°±0.2°, and 25.2°±0.2°.

In another embodiment, the X-ray powder diffraction pattern of the crystalline form of compound 2 further comprises any two or more of the following 2θ values measured using CuKα radiation: 11.1°±0.2°, 13.8°±0.2°, 14.7°±0.2°, 16.7°±0.2°, 19.3°±0.2°, 20.9°±0.2°23.2°±0.2°, and 25.8°±0.2°. In one embodiment, the X-ray powder diffraction pattern comprises all of these 2θ values along 12.6°±0.2°, 15.5°±0.2°, 17.9°±0.2°, 22.1°±0.2°, and 25.2°±0.2°.

In another embodiment, the crystalline form 2A has a melting point with an onset temperature at about 233.3° C. and/or a peak temperature at about 238.1° C. as measured by differential scanning calorimetry.

Figure 5A:
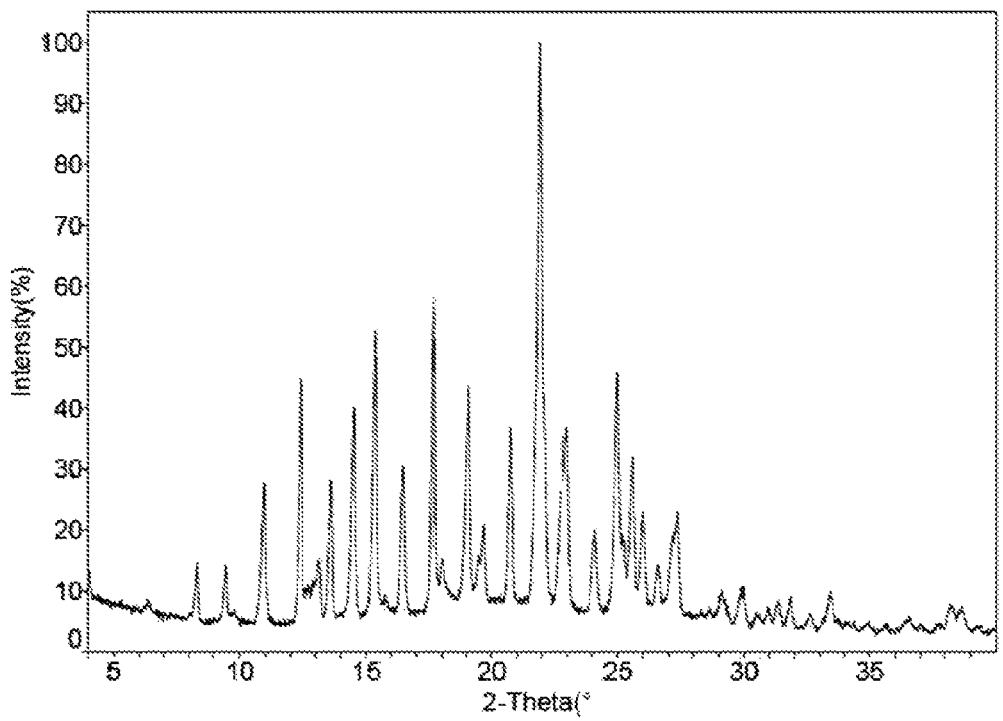

In another embodiment, the crystalline form 2A has an X-ray powder diffraction pattern substantially as depicted in FIG. 5.

Figure 7:
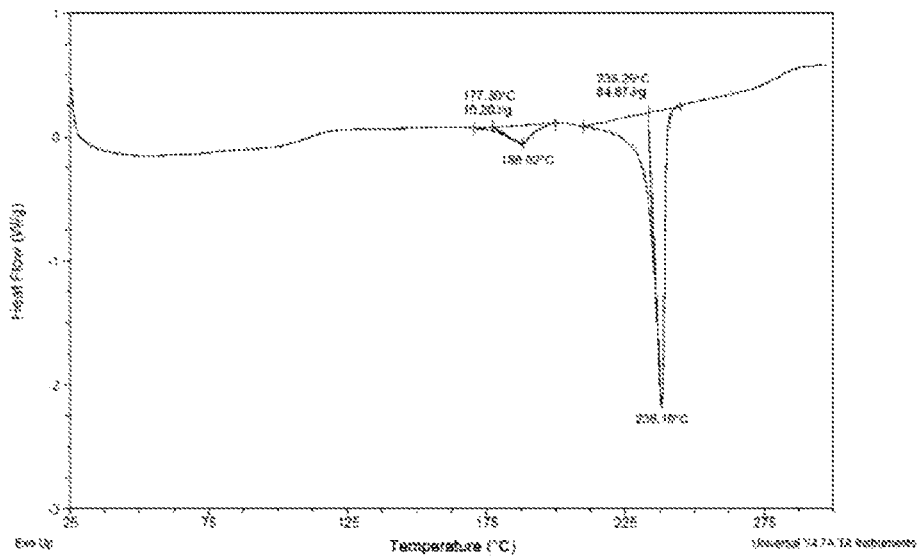
FIG. 7 illustrates DSC thermogram of compound 2 (Form 2A).

In another embodiment, the crystalline form 2A has a differential scanning calorimetric thermogram substantially as depicted in FIG. 7.

Figure 8:
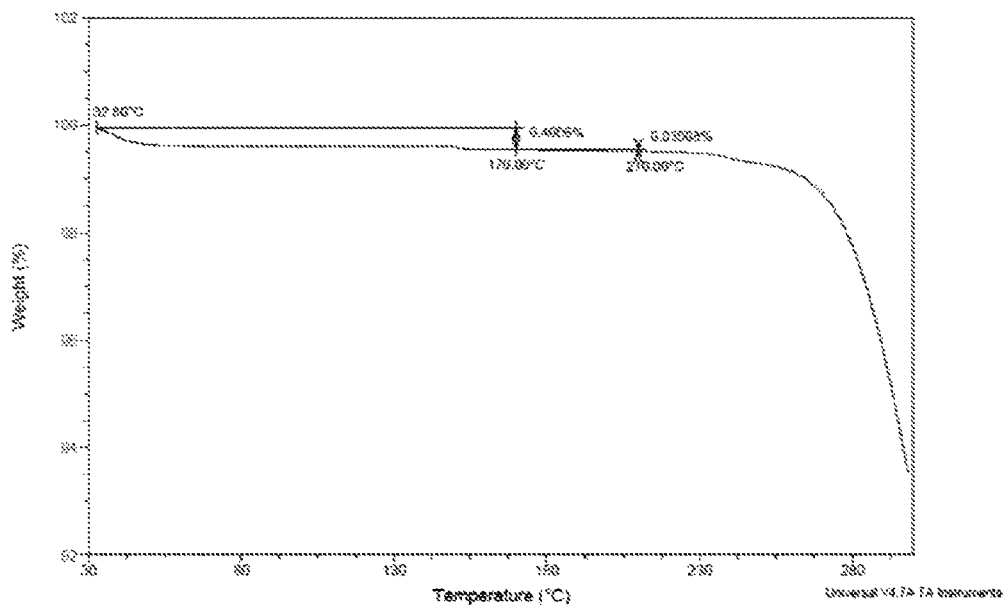
FIG. 8 illustrates TGA thermogram of compound 2 (Form 2A).

In another embodiment, the crystalline form 2A has a thermal gravimetric analysis thermogram substantially as depicted in FIG. 8.

In another embodiment, the X-ray powder diffraction pattern of the crystalline form of compound 2, designated as crystalline Form 2B, has an X-ray powder diffraction pattern comprising any three or more of the following 2θ values measured using CuKα radiation: 9.7°±0.2°, 12.8°±0.2°, 15.7°±0.2°, 18.2°±0.2°, 20.3°±0.2°, 25.1°±0.2°, 25.6°±0.2°, and 26.8°±0.2°. In one embodiment, the X-ray powder diffraction pattern comprises all of these 2θ values.

Figure 9A:
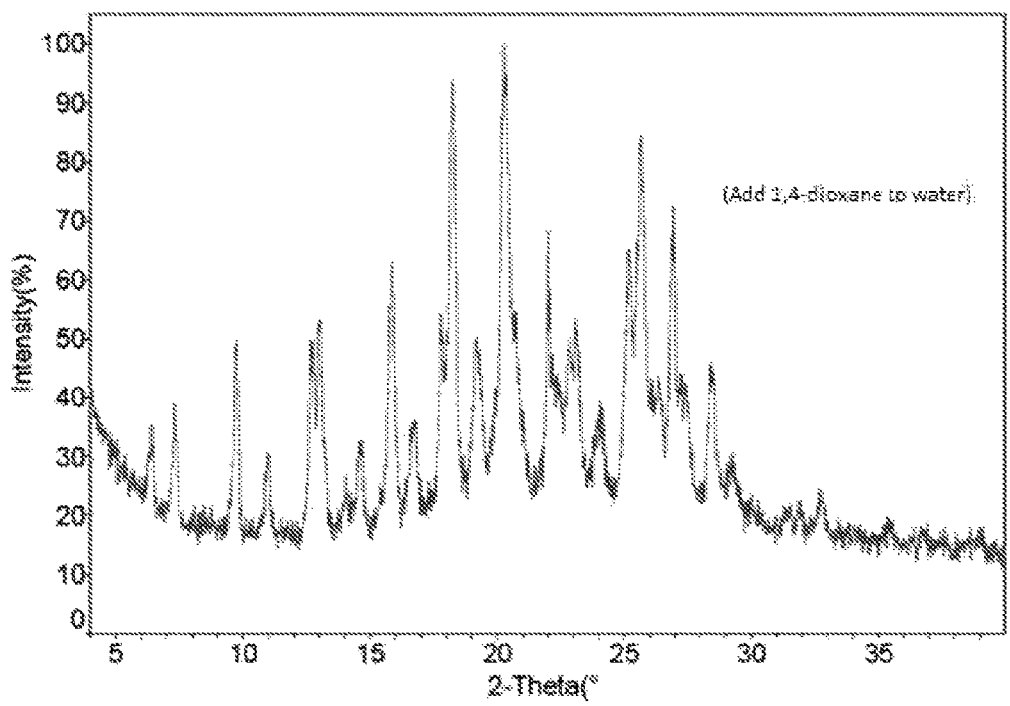
FIGS. 9A and 9B illustrate (FIG. 9A) XRPD pattern of compound 2 (Form 2B)
Figures 9B, 10:
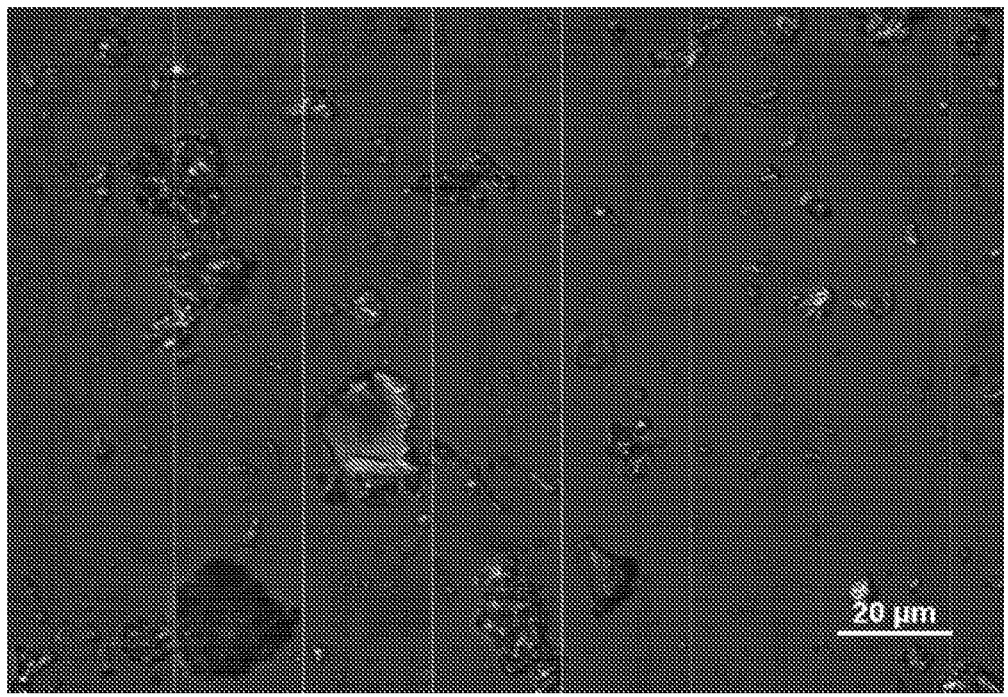
FIG. 10 illustrates PLM image of compound 2 (Form 3) (50×).

In another embodiment, the X-ray powder diffraction pattern of the crystalline form 2B has an X-ray powder diffraction pattern substantially as depicted in FIG. 9.

Figure 12:
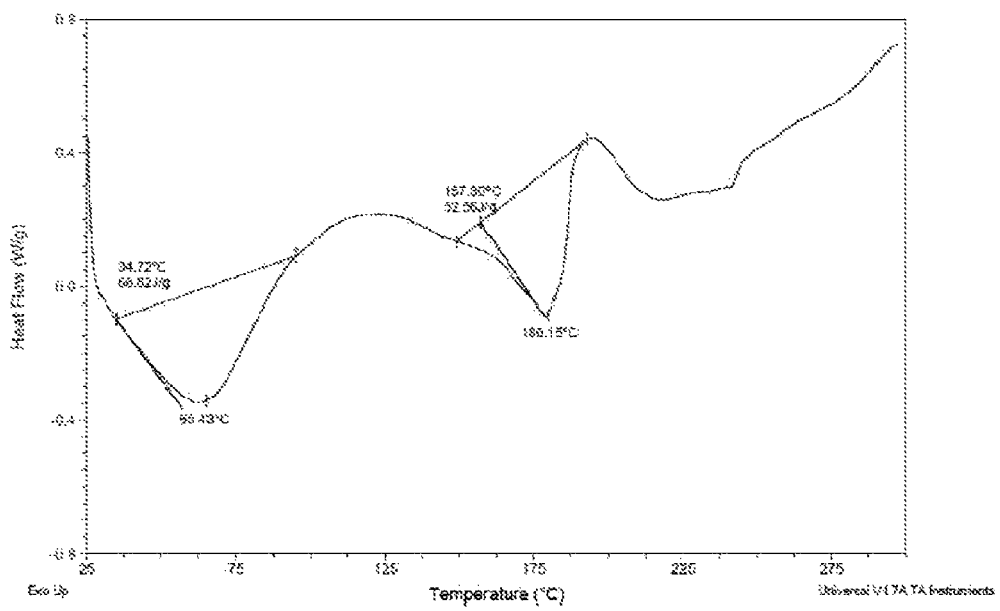
FIG. 12 illustrates DSC thermogram of compound 2 (Form 2B).

In another embodiment, the crystalline form 2B has a differential scanning calorimetric thermogram substantially as depicted in FIG. 12.

Figure 11:
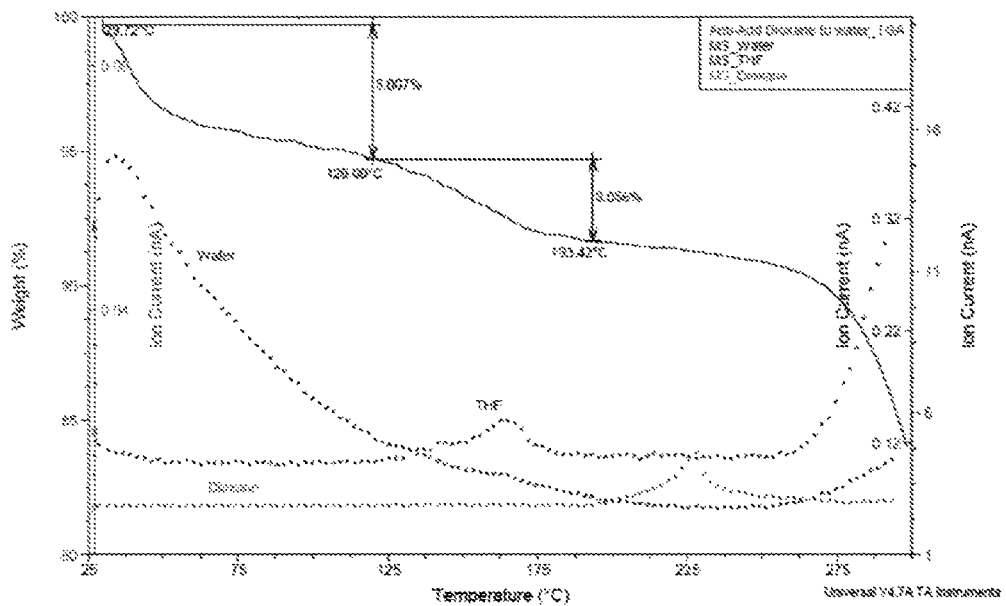
FIG. 11 illustrates TGA-MS of compound 2 (Form 2A).

In another embodiment, the crystalline form 2B has a thermal gravimetric analysis thermogram substantially as depicted in FIG. 11.

In another aspect, the present invention provides a crystalline form of N-(2-(2-(dimethylamino)ethoxy)-4-methoxy-5-((4-(1-methyl-1H-indol-3-yl)pyrimidin-2-yl)amino)phenyl)acrylamide hydrochloride salt (formula 3) having a molar ratio of about 1:1 between hydrochloride acid and free base.

3

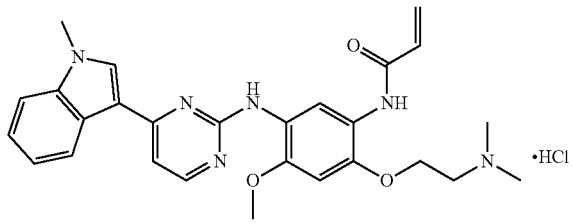

In one embodiment, the crystalline form of compound 3 has an X-ray powder diffraction pattern comprising any three or more of the following 2θ values measured using CuKα radiation: 8.5°±0.2°, 11.2°±0.2°, 18.1°±0.2°, 22.4°±0.2°, 23.5°±0.2°, and 26.3°±0.2°. In one embodiment, the X-ray powder diffraction pattern comprises all of these 2θ values.

In another embodiment, the X-ray powder diffraction pattern of the crystalline form of compound 3 further comprises any two or more of the following 2θ values measured using CuKα radiation: 9.0°±0.2°, 12.7°±0.2°, 16.1°+0.2°, 17.3°±0.2°, 18.7°±0.2°, 20.6°±0.2°, 21.8°±0.2°, and 25.4°±0.2°. In one embodiment, the X-ray powder diffraction pattern comprises all of these 2θ values along 8.5°±0.2°, 11.2°±0.2°, 18.1°±0.2°, 22.4°±0.2°, 23.5°±0.2°, and 26.3°±0.2°.

In another embodiment, the crystalline form of compound 3 has a melting point with an onset temperature at about 266.6° C. and/or a peak temperature at about 269.5° C. as measured by differential scanning calorimetry.

Figure 14A:
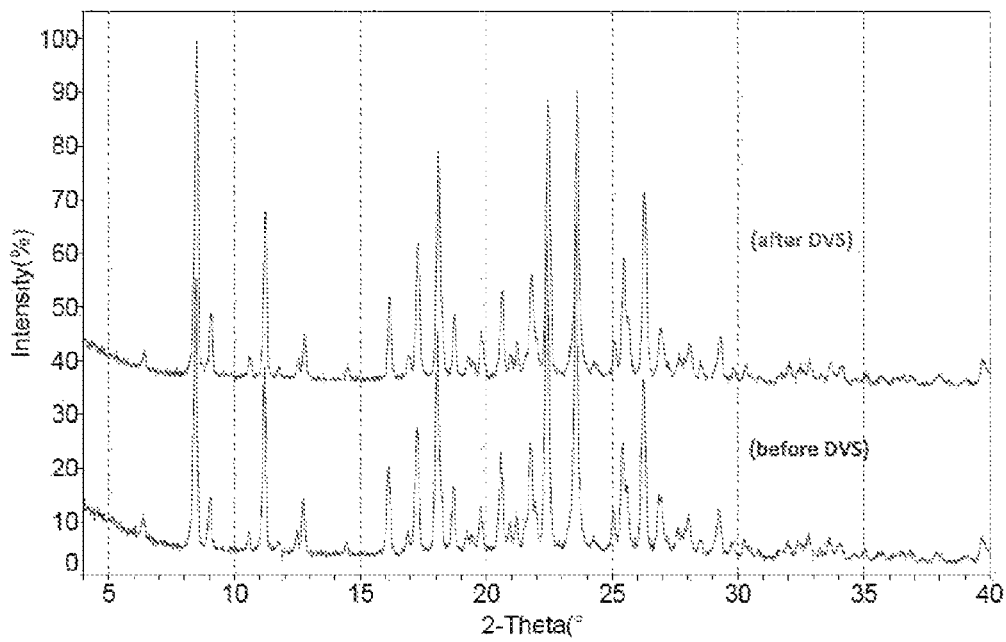
Figure 15:
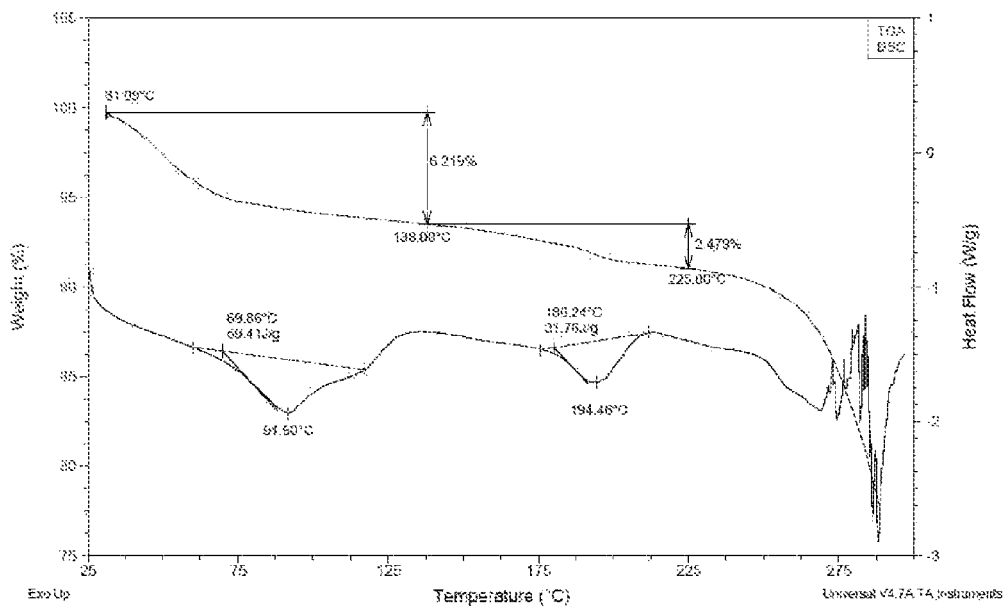
FIG. 15 illustrates Overlay of DSC and TGA thermograms for compound 4.

In another embodiment, the crystalline form of compound 3 has an X-ray powder diffraction pattern substantially as depicted in FIG. 14.

Figure 13:
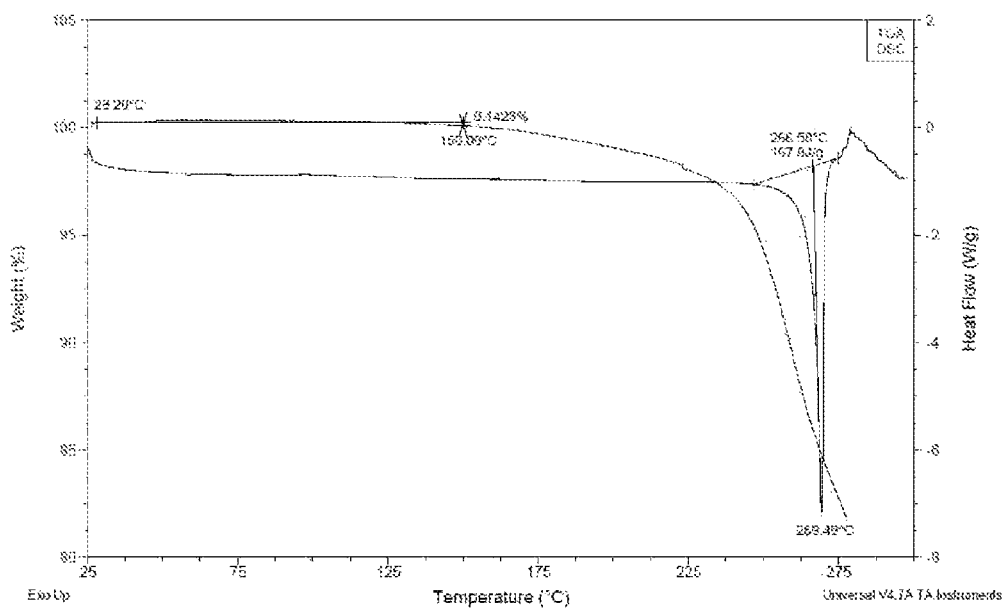
FIG. 13 illustrates Overlay of DSC and TGA thermograms for compound 3.

In another embodiment, the crystalline form of compound 3 has a differential scanning calorimetric thermogram and/or a thermal gravimetric analysis thermogram substantially as depicted in FIG. 13.

In another aspect, the present invention provides a crystalline form of N-(2-(2-(dimethylamino)ethoxy)-4-methoxy-5-((4-(1-methyl-1H-indol-3-yl)pyrimidin-2-yl)amino)phenyl)acrylamide sulfate salt (formula 4) having a molar ratio of about 1:1 between sulfuric acid and free base.

4

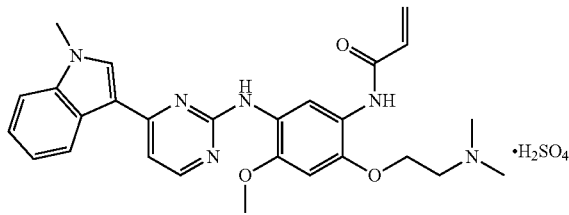

In one embodiment, the crystalline form of compound 4 has an X-ray powder diffraction pattern comprising any three or more of the following 2θ values measured using CuKα radiation: 5.6°±0.2°, 7.3°±0.2°, 11.0°±0.2°, 11.9°±0.2°, 14.3°±0.2°, 18.1°±0.2°, 19.0°±0.2°, 19.6°±0.2°, 19.9°±0.2°, 22.2°±0.2°, 24.9°±0.2°, and 26.3°±0.2°. In one embodiment, the X-ray powder diffraction pattern comprises all of these 2θ values.

In another embodiment, the crystalline form of compound 4 has a melting point with an onset temperature at about 152.3° C. and/or a peak temperature at about 167.1° C. as measured by differential scanning calorimetry.

Figure 16A:
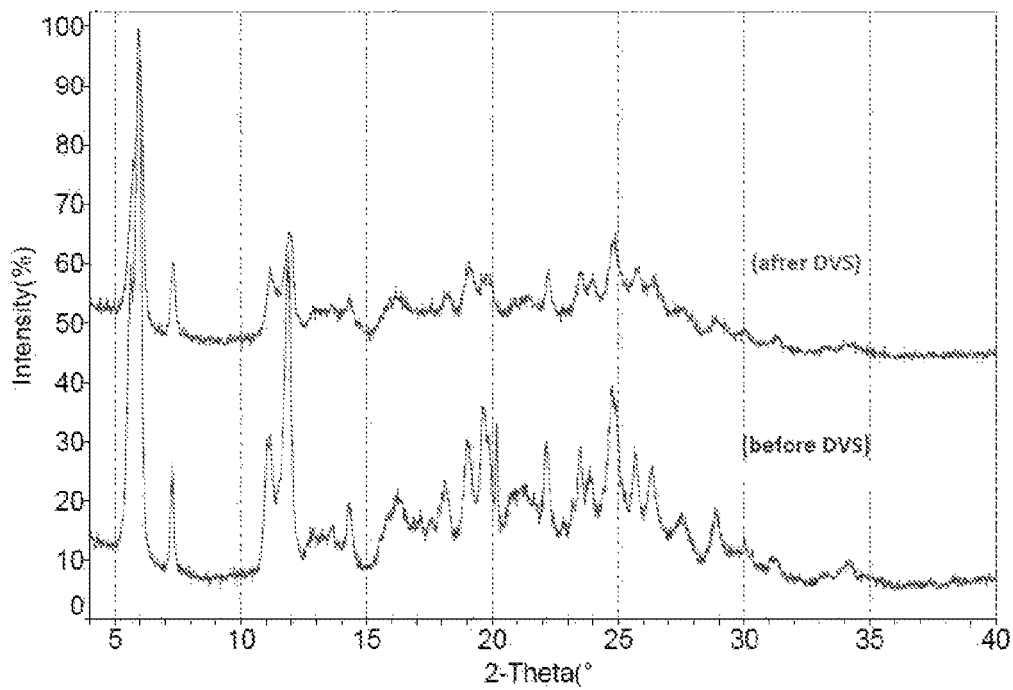

In another embodiment, the crystalline form of compound 4 has an X-ray powder diffraction pattern substantially as depicted in FIG. 16.

Figure 17:
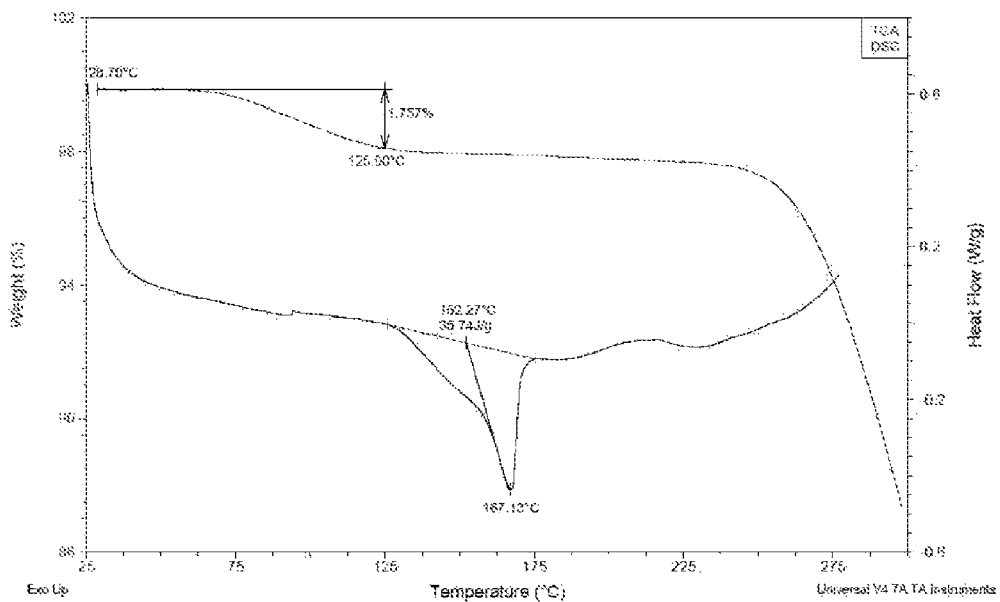
FIG. 17 illustrates Overlay of DSC and TGA thermograms for compound 4.

In another embodiment, the crystalline form of compound 4 has a differential scanning calorimetric thermogram and/or a thermal gravimetric analysis thermogram substantially as depicted in FIG. 17.

In another aspect, the present invention provides a crystalline form of N-(2-(2-(dimethylamino)ethoxy)-4-methoxy-5-((4-(1-methyl-1H-indol-3-yl)pyrimidin-2-yl)amino)phenyl)acrylamide p-toluenesulfonate (p-tosylate) salt (formula 5) having a molar ratio of about 1:1 between p-toluenesulfonic acid and free base.

5

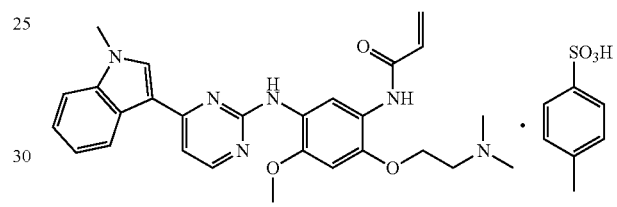

In one embodiment, the crystalline form of compound 5 has an X-ray powder diffraction pattern comprising any three or more of the following 2θ values measured using CuKα radiation: 6.8°±0.2°, 7.3°±0.2°, 10.3°±0.2°, 11.3°±0.2°, 13.1°±0.2°, 15.6°±0.2°, 18.2°±0.2°, 20.5°±0.2°, 19.9°±0.2°, 22.7°±0.2°, 23.3°±0.2°, 27.1°±0.2°, and 29.7°±0.2°. In one embodiment, the X-ray powder diffraction pattern comprises all of these 2θ values.

In another embodiment, the crystalline form of compound 4 has a melting point with an onset temperature at about 152.3° C. and/or a peak temperature at about 167.1° C. as measured by differential scanning calorimetry.

Figure 18A:
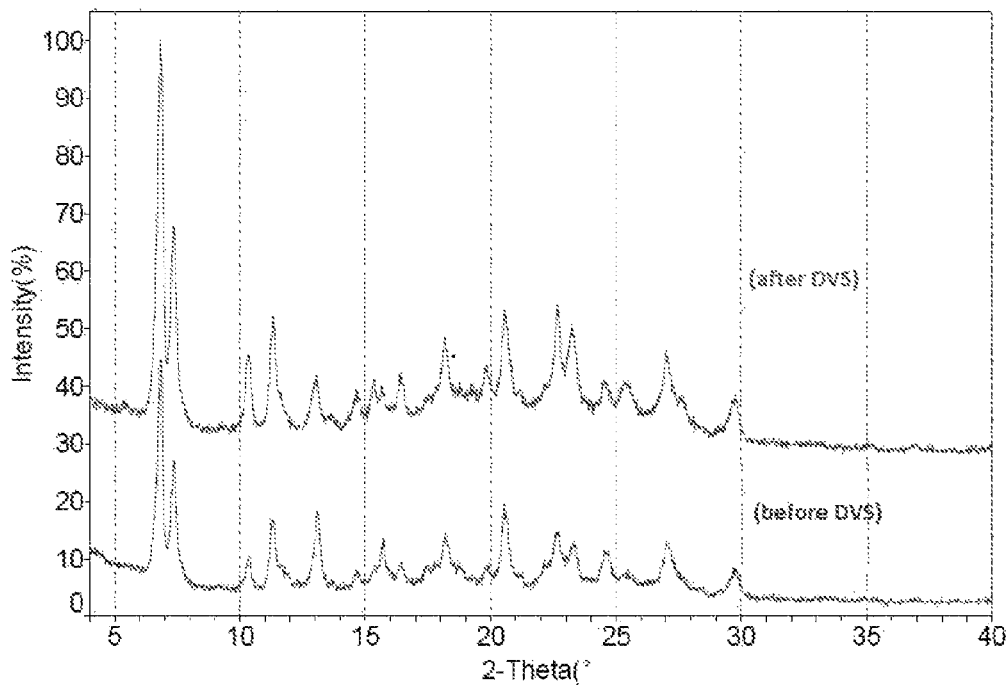
FIGS. 18A and 18B illustrate (FIG. 18A) Overlay of XRPD patterns for compound 5 before (bottom) and after (top) DVS.

In another embodiment, the crystalline form of compound 4 has an X-ray powder diffraction pattern substantially as depicted in FIG. 18.

Figures 18B, 19:
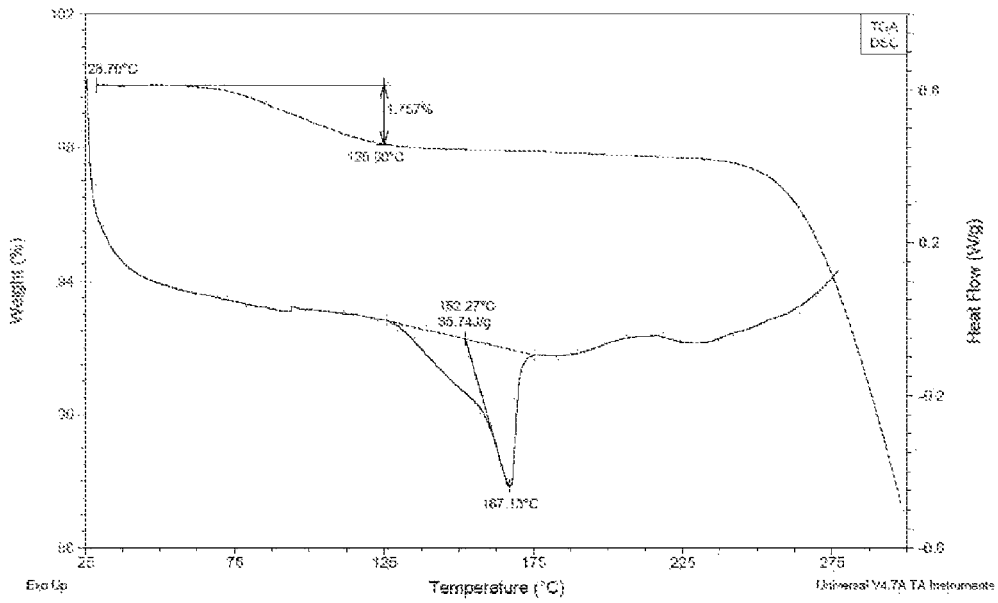
FIG. 19 illustrates Overlay of DSC and TGA thermograms for compound 5.
Figure 20:
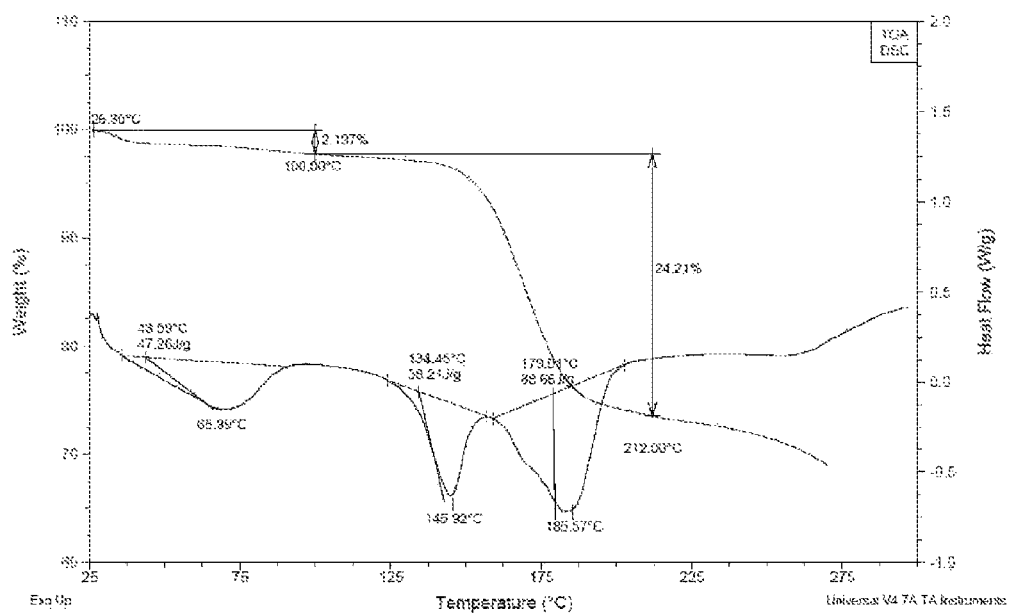
FIG. 20 illustrates Overlay of DSC and TGA thermograms for compound 6.

In another embodiment, the crystalline form of compound 4 has a differential scanning calorimetric thermogram and/or a thermal gravimetric analysis thermogram substantially as depicted in FIG. 19.

In another aspect, the present invention provides a crystalline form of N-(2-(2-(dimethylamino)ethoxy)-4-methoxy-5-((4-(1-methyl-1H-indol-3-yl)pyrimidin-2-yl)amino)phenyl)acrylamide citrate salt (formula 6) having a molar ratio of about 1:1 between citric acid and free base.

6

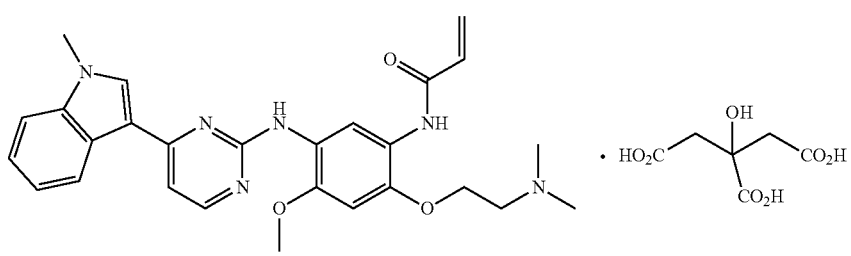

In one embodiment, the crystalline form of compound 6 has an X-ray powder diffraction pattern comprising any three or more of the following 2θ values measured using CuKα radiation: 5.9°±0.2°, 8.0°±0.2°, 13.2°±0.2°, 19.0°±0.2°, 25.6°±0.2°, and 26.5°±0.2°. In one embodiment, the X-ray powder diffraction pattern comprises all of these 2θ values.

In another embodiment, the X-ray powder diffraction pattern of the crystalline form of compound 6 further comprises any two or more of the following 2θ values measured using CuKα radiation: 12.6°±10.2°, 16.0°±0.2°, 16.6°±0.2°, 17.0°±0.2°, 18.5°±0.2°, 20.3°±0.2°, 23.2°±0.2°, and 25.8°±0.2°. In one embodiment, the X-ray powder diffraction pattern comprises all of these 2θ values along 5.9°±0.2°, 8.0°±0.2°, 13.2°±0.2°, 19.0°±0.2°, 25.6°±0.2°, and 26.5°±0.2°.

In another embodiment, the crystalline form of compound 6 has an X-ray powder diffraction pattern substantially as depicted in FIG. 22.

Figure 21A:
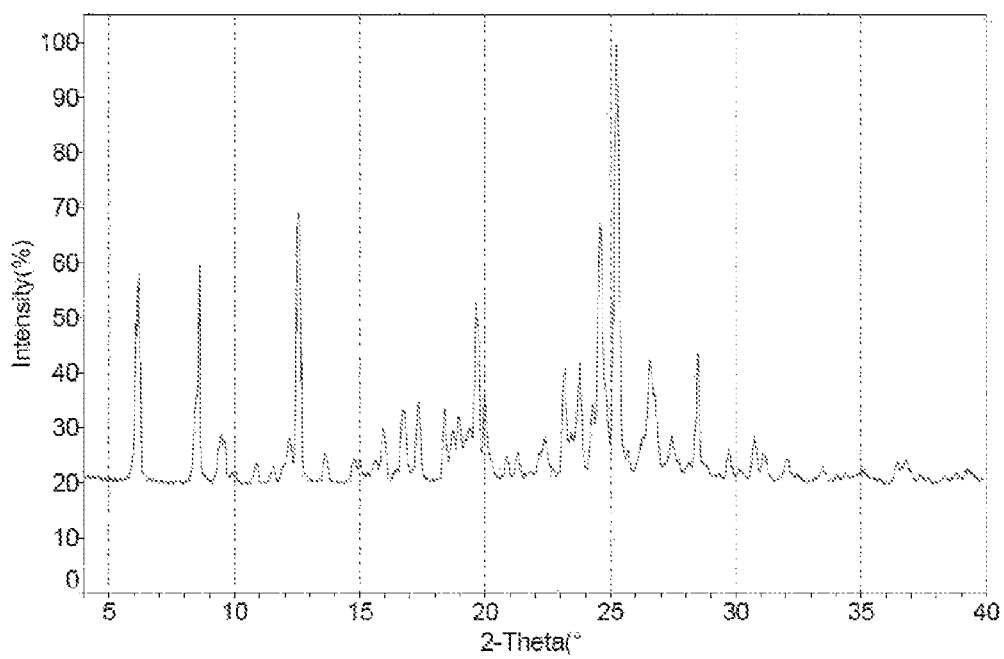

In another embodiment, the crystalline form of compound 6 has a differential scanning calorimetric thermogram and/or a thermal gravimetric analysis thermogram substantially as depicted in FIG. 21.

In another aspect, the present invention provides a pharmaceutical composition comprising a crystalline form according to any of embodiments disclosed here, or a combination thereof, and a pharmaceutically acceptable carrier, adjuvant, diluent, and/or vehicle.

In another aspect, the present invention provides a method of treating a disease or disorder associated with an EGFR activity, comprising administration of a therapeutically effective amount of a crystalline form according to any one of the embodiments disclosed herein, or a combination thereof, or a pharmaceutical composition thereof, to a patient in need of treatment.

In one embodiment, the disease or disorder is associated with one or more mutants of EGFR.

In another embodiment, the mutant or mutants of EGFR are selected from L858R activating mutants L858R, delE746-A750, G719S; the Exon 19 deletion activating mutant; and the T790M resistance mutant.

In another embodiment, the disease or disorder is a cancer.

In another embodiment, the cancer is selected from brain cancer, lung cancer, kidney cancer, bone cancer, liver cancer, bladder cancer, head and neck cancer, esophageal cancer, stomach cancer, colon cancer, rectum cancer, breast cancer, ovarian cancer, melanoma, skin cancer, adrenal cancer, cervical cancer, lymphoma, and thyroid tumors and their complications.

In another embodiment, the cancer is brain cancer or lung cancer.

In another embodiment, the cancer is a metastatic brain cancer.

In another embodiment, the any embodiment of the method of treating diseases or disorders is used in combination with administering to the patient a second therapeutic agent.

In another embodiment, the second therapeutic agent is a chemotherapeutic agent.

In another embodiment, the second therapeutic agent is a different EGFR modulator.

In another aspect, the present invention provides a method of inhibiting a mutant of EGFR in a subject, comprising contacting a biological sample of said subject with a crystalline forms of compounds according to any embodiments disclosed herein, or a combination thereof, or a pharmaceutical composition thereof.

In another aspect, the present invention provides use of a crystalline form according to any embodiments disclosed herein, or a combination or mixture thereof, in the manufacture of a medicament for treatment of a disease or disorder associated with an EGFR activity.

In one embodiment of this aspect, the disease or disorder is a cancer selected from the group consisting of brain cancer, lung cancer, kidney cancer, bone cancer, liver cancer, bladder cancer, head and neck cancer, esophageal cancer, stomach cancer, colon cancer, rectum cancer, breast cancer, ovarian cancer, melanoma, skin cancer, adrenal cancer, cervical cancer, lymphoma, and thyroid tumors and their complications.

In another embodiment of this aspect, the disease or disorder is brain cancer or lung cancer.

In another aspect, the present invention provides processes of preparing a crystalline form according to any embodiments disclosed herein as substantially described and shown.

Pharmaceutical formulations may be presented in unit dose forms containing a predetermined amount of active ingredient per unit dose. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford effective results without causing substantial harmful or deleterious side effects.

When the compositions of this disclosure comprise a combination of a crystalline form of compound 1 or salt of the present disclosure and one or more, preferably one or two, additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example, by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection is preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Where appropriate, dosage unit formulations for oral administration can be microencapsulated. The formulation can also be prepared to prolong or sustain the release as for example by coating or embedding particulate material in polymers, wax, or the like.

It should be understood that in addition to the ingredients particularly mentioned above, the formulations may include other agents conventional in the art having regard to the type of formulation in question, for example those suitable for oral administration may include flavoring agents.

The term "patient" or "subject" includes both human and other mammals.

The term "mammal" or "mammalian animal" includes, but is not limited to, humans, dogs, cats, horses, pigs, cows, monkeys, rabbits and mice. The preferred mammals are humans.

The term "therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, or other factors of the subject to be treated. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term "treating" or "treatment" refers to: (i) inhibiting the disease, disorder, or condition, i.e., arresting its development; (ii) relieving the disease, disorder, or condition, i.e., causing regression of the disease, disorder, and/or condition; or (iii) preventing a disease, disorder or condition from occurring in a subject that may be predisposed to the disease, disorder, and/or condition but has not yet been diagnosed as having it. Thus, in one embodiment, "treating" or "treatment" refers to ameliorating a disease or disorder, which may include ameliorating one or more physical parameters, though may be indiscernible by the subject being treated. In another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

When the term "about" is applied to a parameter, such as amount, temperature, time, or the like, it indicates that the parameter can usually vary by ±10%, preferably within ±5%, and more preferably within ±2%. As would be understood by a person skilled in the art, when a parameter is not critical, a number provided in the Examples is often given only for illustration purpose, instead of being limiting.

The term "a," "an," or "the," as used herein, represents both singular and plural forms. In general, when either a singular or a plural form of a noun is used, it denotes both singular and plural forms of the noun.

The following non-limiting Examples further illustrate certain aspects of the present invention.

EXAMPLES

Example 1

N-(2-(2-(Dimethylamino)ethoxy)-4-methoxy-5-((4-(1-methyl-1H-indol-3-yl)pyrimidin-2-yl)amino)phenyl)acrylamide (1)

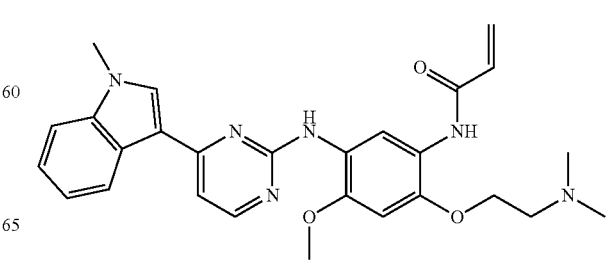

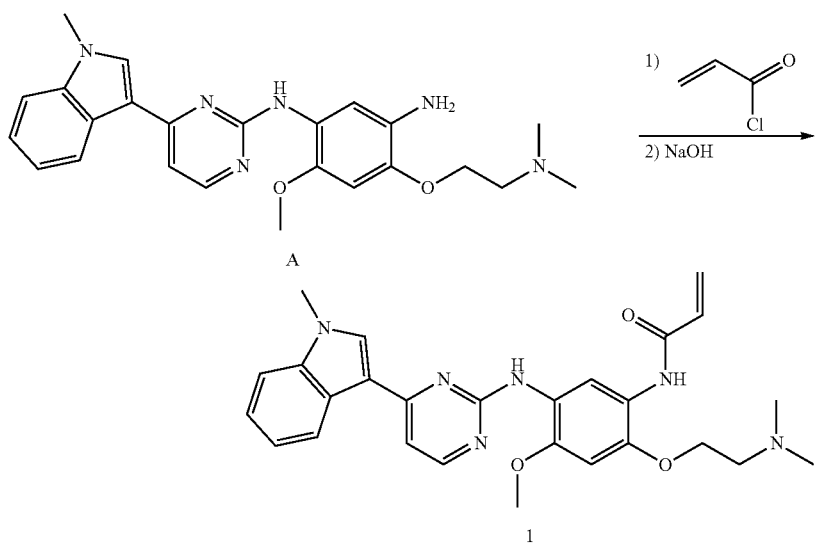

A

1

Step 1. A solution of 4-(2-(dimethylamino)ethoxy)-6-methoxy-N-1-(4-(1-methyl-1H-indol-3-yl)pyrimidin-2-yl)benzene-1,3 diamine (A, prepared as in International Application No. PCT/US15/65286; 1 equiv, 16.8 g, 26.2 mmol) in THF (550 mL) and water (120 mL) was cooled to 0-5° C. Acryloyl chloride (1.0 equiv., 3.3 mL) was added dropwise over 30 minutes. After 2 hours, additional acryloyl chloride (0.4 mL) was added over 10 minutes and the mixture was stirred for 1 h. NaOH (2 equiv., 2.8 g, 68.0 mmol) was added, and the mixture was stirred for 30 minutes, and then partially concentrated to remove THF. The aqueous phase was extracted with dichloromethane (900 mL), and the organic phase was dried $Na_2SO_4$ and concentrated. The crude product was purified via column chromatography (silica gel; dichloromethane/MeOH, 80:1 to 20:1 gradient) to afford 1 (14.0 g). Further purification of 1, according to Step 2, was necessary in order to obtain compound 1.

Step 2. To a solution of 1, prepared as in Step 1, (1 eq, 22.5 g, 46.3 mmol), in 850 mL of THF was added NaOH (9 g dissolved in 203 mL of $H_2O$) over 5 min. The mixture was heated to 60° C. with stirring for 50 min, then cooled to 10-20° C. and 1N HCl (180 mL) was added over 20 min. The layers were separated and the aqueous phase was extracted with dichloromethane (2×400 mL). The organic phases were combined, dried ($Na_2SO_4$) and concentrated. The crude product was purified via column chromatography (silica gel; 20:1 dichloromethane/MeOH) to afford a solid, which was dissolved in dichloromethane/heptane (2:3) then concentrated to afford 19.5 g of compound 1 as a crystalline solid. $^1$H NMR (400 MHz, $CD_3OD$) δ ppm 2.42 (s, 6H), 2.80 (br t, J=5.0 Hz, 2H), 3.98 (s, 3H), 3.92 (s, 3H), 4.21 (br t, J=5.0 Hz, 2H), 5.79 (dd, J=10.2, 1.4 Hz, 1H), 6.39 (dd, J=16.9, 1.4 Hz, 1H), 6.64 (dd, J=16.9, 10.2 Hz, 1H), 6.83 (s, 1H), 7.15-7.30 (m, 3H), 7.46 (d, J=7.6 Hz, 1H), 8.16-8.30 (m, 2H), 8.52 (s, 1H), 9.29 (s, 1H).

Figure 2:
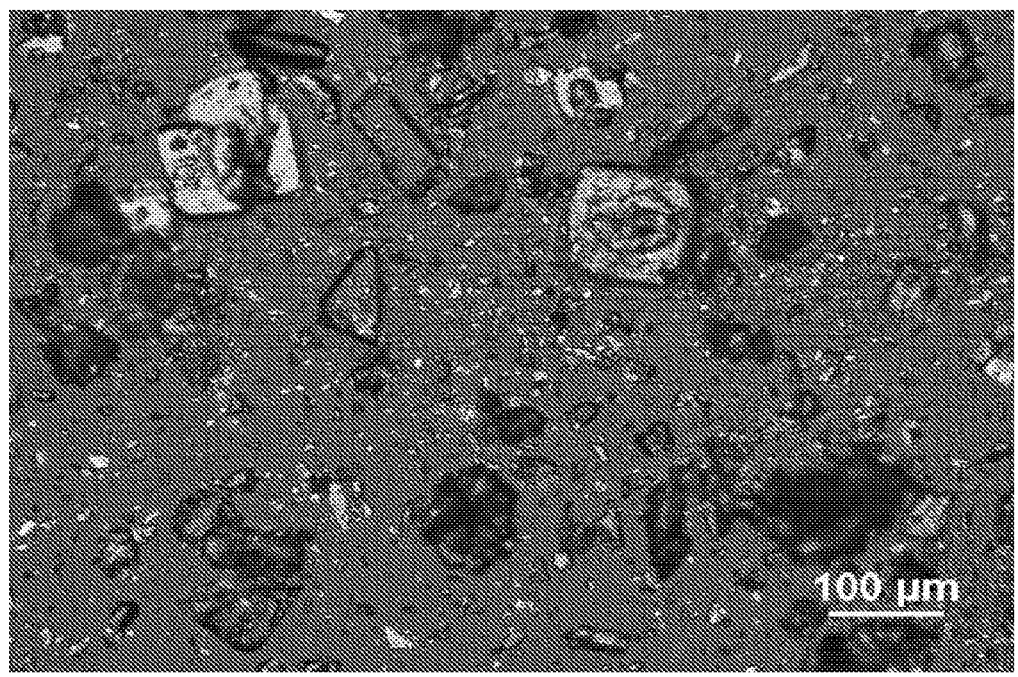
FIG. 2 illustrates PLM image of compound 1 (free base).

The crystalline form of compound 1 was characterized by X-ray powder diffraction (XRPD), polarized light microscopy (PLM), differential scanning calorimetry (DSC) and thermogravimetric analysis (TGA); FIGS. 1-4. It is a crystalline powder that displays birefringence and irregular shape with some agglomerations under the PLM (FIG. 2). The crystalline form of compound 1 has a melting point with onset temperature at 169.6° C., ~0.35% weight loss before the melting point and ~1.62% weight loss from 137° C. to 185° C. (FIGS. 3-4).

Example 2

N-(2-(2-(Dimethylamino)ethoxy)-4-methoxy-5-((4-(1-methyl-1H-indol-3-yl)pyrimidin-2-yl)amino)phenyl)acrylamide methanesulfonate (1:1) (2)

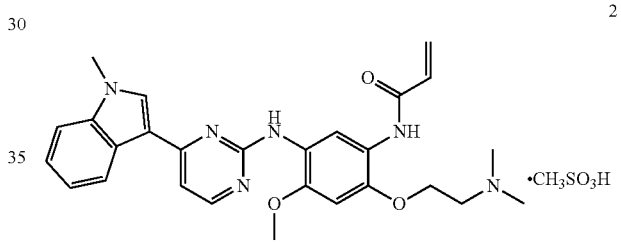

2

To a solution of 100 mg of compound 1 (free base) in 4 mL of THF was added a solution of 21.7 mg of methanesulfonic acid in 0.164 mL of water, and the solution was stirred at room temperature overnight. The precipitate was isolated by centrifugation at 8000 rpm for 5 mins. After drying under vacuum at 30° C. overnight, 60 mg of methanesulfonate salt, crystalline Form 2A, was obtained. $^1$H NMR (400 MHz, $CD_3OD$) δ ppm 2.73 (s, 3H), 3.06 (s, 6H), 3.65-3.72 (m, 2H), 3.94 (s, 3H), 4.00 (s, 3H), 4.54-4.60 (m, 2H), 5.86 (br d, J=10.0 Hz, 1H), 6.40-6.48 (m, 1H), 6.56-6.66 (m, 1H), 6.98 (s, 1H), 7.20-7.34 (m, 3H), 7.50 (d, J=8.0 Hz, 1H), 8.11 (br d, J=6.0 Hz, 1H), 8.35 (br d, J=7.8 Hz, 1H), 8.42 (s, 1H), 8.50 (br s, 1H). Anal. Calcd. for $C_{28}H_{34}N_6O_6S$: C, 57.72; H, 5.88; N, 14.42; O, 16.47; S, 5.50. Found: C, 57.76; H, 5.85; N, 14.45; O, 16.34; S, 5.60; $C_{27}H_{30}N_6O_3 \cdot 1.0$ $CH_3SO_3H$.

Figure 6:
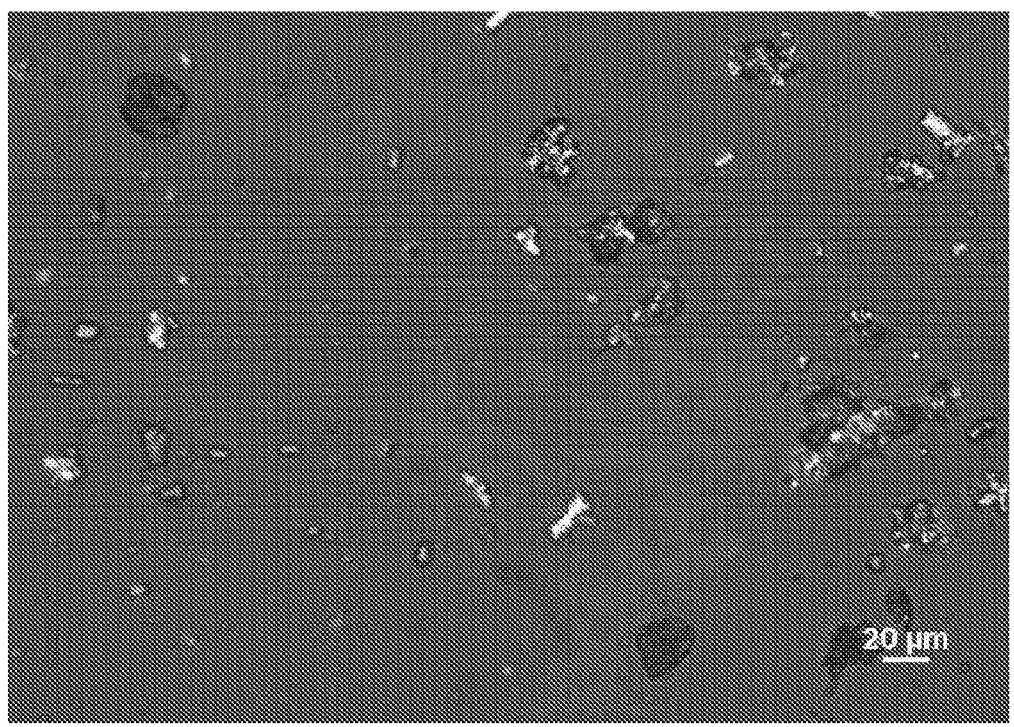
FIG. 6 illustrates PLM image of compound 2 (Form 2A) (50×).

Form 2A is a beige crystalline powder; its XRPD pattern is shown in FIG. 5. It shows birefringence and has a melting point with onset temperature at 233.3° C., ~0.40% weight loss before the melting point and 0.035% weight loss from 170° C. to 210° C. (PLM, FIG. 6; DSC, FIG. 7; TGA, FIG. 8).

A polymorph screening study was performed on Form 2A by the slurry, solvent-thermal heating/cooling, anti-solvent precipitation, solid heating-cooling and grinding methods. One new crystal form, Form 2B, was found. Form 2B may be a hydrate form of Form 2A and shows low crystallinity, low melting point and high weight loss compared with the Form 2A. XRPD, PLM, DSC, and TGA-MS analyses of Form 2B are shown in FIGS. 9-12.

Example 3

N-(2-(2-(Dimethylamino)ethoxy)-4-methoxy-5-((4-(1-methyl-1H-indol-3-yl)pyrimidin-2-yl)amino)phenyl)acrylamide hydrochloride (1:1) (3)

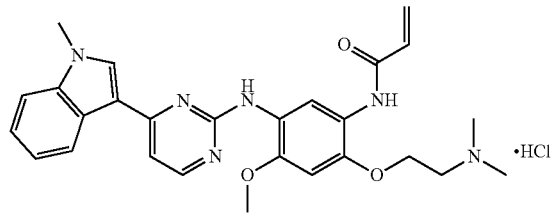

3

A dilute hydrochloric acid solution was prepared by dissolving 650.6 mg of a 38% HCl solution in 5 mL of THF. This solution (0.167 mL) was added to a solution of 100 mg of compound 1 (free base) dissolved in 4 mL of THF. The solution was stirred at room temperature overnight. The resulting solid precipitate was isolated by centrifugation at 8000 rpm for 5 min. After drying under vacuum at 30° C. overnight, 70 mg of HCl salt (3) was obtained. An overlay of DSC and TGA curves is shown in FIG. 13, and an overlay of XRPD patterns before and after DVS is shown in FIG. 14.

The methods of Examples 1 and 2 were used to prepare sulfate (4), tosylate (5), and citrate (6) salts.

Example 4

N-(2-(2-(Dimethylamino)ethoxy)-4-methoxy-5-((4-(1-methyl-1H-indol-3-yl)pyrimidin-2-yl)amino)phenyl)acrylamide sulfate (1:1) (4)

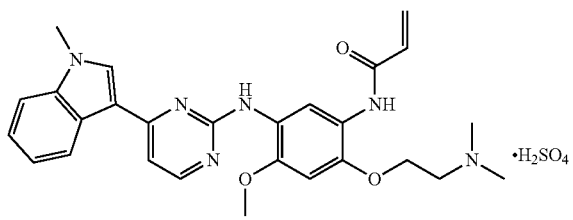

4

Example 5

N-(2-(2-(Dimethylamino)ethoxy)-4-methoxy-5-((4-(1-methyl-1H-indol-3-yl)pyrimidin-2-yl)amino)phenyl)acrylamide p-toluenesulfonate (1:1) (5)

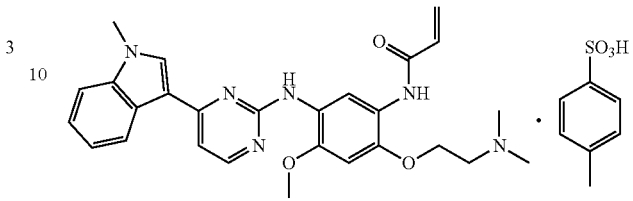

5

$^1$HNMR (400 MHz, DMSO-$d_6$) δ ppm 2.29 (s, 3H), 2.92 (s, 6H), 3.50-3.62 (m, 2H), 3.89 (s, 3H), 3.91 (s, 3H), 4.37-4.48 (m, 2H), 5.79 (dd, J=10.2, 1.5 Hz, 1H), 6.29 (dd, J=16.9, 1.5 Hz, 1H), 6.59 (br dd, J=16.9, 10.2 Hz, 1H), 6.94 (s, 1H), 7.09-7.17 (m, 3H), 7.18-7.27 (m, 2H), 7.48 (d, J=8.0 Hz, 2H), 7.52 (d, J=8.0 Hz, 1H), 7.95 (s, 1H), 8.26-8.38 (m, 2H), 8.48 (s, 1H), 8.66 (s, 1H), 9.38 (s, 1H).

Example 6

N-(2-(2-(Dimethylamino)ethoxy)-4-methoxy-5-((4-(1-methyl-1H-indol-3-yl)pyrimidin-2-yl)amino)phenyl)acrylamide citrate (1:1) (6)

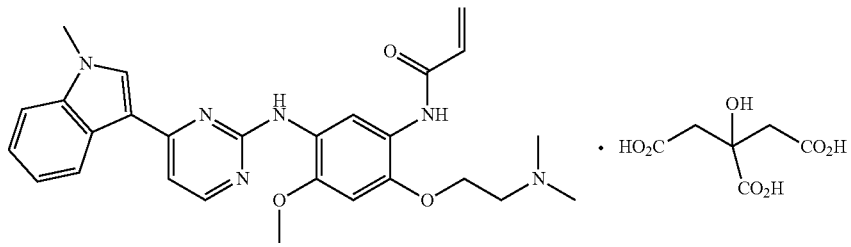

6

$^1$H NMR (400 MHz, DMSO-$d_6$) δ ppm 2.58 (br d, J=17.8 Hz, 4H), 2.70 (s, 6H), 3.21 (br t, J=4.9 Hz, 2H), 3.88 (s, 3H), 3.90 (s, 3H), 4.36 (br t, J=4.9 Hz, 2H), 5.78 (dd, J=10.2, 1.6 Hz, 1H), 6.28 (dd, J=16.9, 1.6 Hz, 1H), 6.56 (dd, J=16.9, 10.2 Hz, 1H), 6.94 (s, 1H), 7.11-7.28 (m, 3H), 7.52 (d, J=8.0 Hz, 1H), 7.93 (s, 1H), 8.23-8.38 (m, 2H), 8.50 (s, 1H), 8.73 (s, 1H), 9.55 (s, 1H).

Summary of XRPD/DSC/TGA Analysis of Crystalline Forms of Compounds 2 to 6

Based on the XRPD/DSC/TGA results of the five salts, namely compounds 3 (HCl), 4 (sulfate), 2 (mesylate), 5 (tosylate) and 6 (citrate), Compound 3 showed the best crystallinity, the highest melting point (266.6° C.) and the least weight loss 0.14%. Compounds 4-6 showed a melting point range from 130° C. to 180° C. with variable weigh loss from 1.8% to 6.2% on TGA. The degree of crystallinity is compound 3 (HCl)>4 (sulfate)≈2 (mesylate)≈4 (tosylate)>6 (citrate). According to DVS results, compounds 3 and 5 could be classified as slightly hygroscopic (0.76% and 1.86% weight gain from 0 to 80% RH, respectively) while compounds 4 and 2 are hygroscopic (10.60% and 14.44% weight gain from 0 to 80% RH, respectively). No form transformation was observed after DVS test for any of the salts.

TABLE 1

Detailed Information of Salt Forms

| Ex. | Compound (Form) | DSC 1st peak (° C.)/H (J/g) | DSC 2nd peak (° C.)/H (J/g)$^a$ | DSC 3rd peak (° C.)/H (J/g) | TGA (wt % loss) | DVS Sorption (%) | Stoichiometry (free base:acid) |
|---|---|---|---|---|---|---|---|
| 1 | 1 (free base) | 169.6/78.7 | — | — | 0.35 (30.6-137.0° C.) 1.6 (137.0-185.0° C.) | — | — |
| 2 | 2 (Form 2A) (methanesulfonate) | 239.8/105.3 | — | — | 0.27 (26.5-210.0° C.) | 0.91 | 1:1.0 |
| 3 | 3 (Form 2B) (methanesulfonate) | 31.2/65.0 | 159.1/26.3 | — | 2.8 (29.7-144.0° C.) 0.51 (144.0-204.0° C.) | 14.44 | 1:1.1 |
| 4 | 3 (hydrochloride) | 266.6/167.8 | — | — | 0.14 (28.2-150.0° C.) | 0.76 | 1:1.0 |
| 5 | 4 (sulfate) | 69.9/59.4 | 180.2/31.8 | — | 6.2 (31.1-138.0° C.) 2.5 (138.0-225.0° C.) | 10.60 | 1:1.0 |
| 6 | 5 (p-toluenesulfonate) | 152.3/35.7 | — | — | 1.8 (28.7-125.0° C.) | 1.86 | 1:1.0 |
| 7 | 6 (citrate) | 43.6/47.3 | 134.5/38.2 | 179.0/88.7 | 2.2 (26.3-100.0° C.) 24.2 (100.0-212.0° C.) | — | 1:1.0 |

"—" indicates either no data available or not determined

TABLE 2

Solubility Data for Various Salt Forms

| Example | Salt | Solubility (mg/mL) | Final pH | HPLC Purity (%) |
|---|---|---|---|---|
| 1 | 1 (free base) | 0.05 | 6.2 | — |
| 2 | 2 (methanesulfonate) | >53 | 4.9 | 95.7 |
| 4 | 3 (hydrochloride) | 0.81 | 6.0 | 91.2 |
| 5 | 4 (sulfate) | >79 | 2.4 | 99.5 |
| 6 | 5 (p-toluenesulfonate) | 0.53 | 5.8 | 92.8 |
| 7 | 6 (citrate) | 6.9 | 4.6 | 97.1 |

Definitions

X-ray Powder Diffractometer (XRPD)
Differential Scanning Calorimetry (DSC)
Thermal Gravimetric Analysis (TGA)
Polarized Light Microscopy (PLM)
Dynamic Vapor Sorption (DVS)
Thermogravimetric Analyzer/Mass Spectrometer (TGA-MS)

TABLE 3

Instrumentation

| Name | Model | Manufacture |
|---|---|---|
| X-ray Powder Diffractometer (XRPD) | D8 advance | Bruker |
| Polarized Light Microscopy (PLM) | LV100 PL | Nikon |
| Differential Scanning Calorimetry (DSC) | Q2000 | TA |
| Thermal Gravimetric Analysis (TGA) | Q5000IR | TA |
| Mass Spectrometer (MS) | QGA | Hiden |
| Dynamic Vapor Sorption System (DVS) | Advantage-1 | SMS |
| Nuclear Magnetic Resonance (NMR) | AVANCE III (400 MHz) | Bruker |
| High Performance Liquid Chromatograph (HPLC) | Agilent 1200 and 1260 | Agilent |

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims.

The invention claimed is:

1. A crystalline form of the compound of formula 1, namely N-(2-(2-(dimethylamino)ethoxy)-4-methoxy-5-((4-(1-methyl-1H-indol-3-yl)pyrimidin-2-yl)amino)phenyl) acrylamide (free base), having an X-ray powder diffraction pattern comprising the following 2θ values measured using CuKα radiation: 8.5°±0.2°, 16.7°±0.2°, and 25.2°±0.2°

1

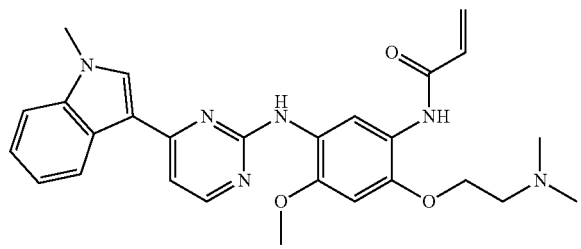

2. The crystalline form of claim 1, wherein the X-ray powder diffraction pattern further comprises two or more of the following 2θ values measured using CuKα radiation: 9.5°±0.2°, 12.2°±0.2°, 12.5°±0.2°, 15.7°±0.2°, 16.0°±0.2°, 19.4°±0.2°, 19.7°±0.2°, 20.0°±0.2°, 23.2°±0.2°, 24.4°±0.2°, and 28.5°±0.2°.

3. The crystalline form of claim 1, having a melting point with an onset temperature at about 169.6° C. and/or a peak temperature at about 171.7° C. as measured by differential scanning calorimetry.

4. A crystalline form of N-(2-(2-(dimethylamino)ethoxy)-4-methoxy-5-((4-(1-methyl-1H-indol-3-yl)pyrimidin-2-yl)amino)phenyl)acrylamide methanesulfonate salt (formula 2) having a molar ratio of about 1:1 between methanesulfonic acid and free base, designated as Form 2A, having an X-ray powder diffraction pattern comprising the following 2θ values measured using CuKα radiation: 12.6°±0.2°, 15.5°±0.2°, 17.9°±0.2°, 22.1°±0.2°, and 25.2°±0.2°

2

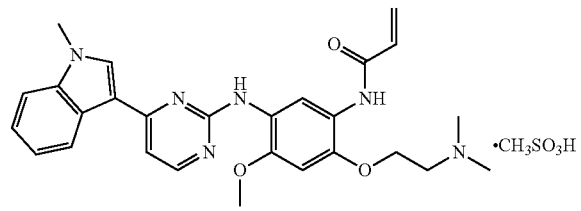

5. The crystalline form of claim 4, wherein the X-ray powder diffraction pattern further comprises two or more of the following 2θ values measured using CuKα radiation: 11.1°±0.2°, 13.8°±0.2°, 14.7°±0.2°, 16.7°±0.2°, 19.3°±0.2°, 20.9°±0.2°, 23.2°±0.2°, and 25.8°±0.2°.

6. The crystalline form of claim 4, having a melting point with an onset temperature at about 233.3° C. and/or a peak temperature at about 238.1° C. as measured by differential scanning calorimetry.

7. A crystalline form of N-(2-(2-(dimethylamino)ethoxy)-4-methoxy-5-((4-(1-methyl-1H-indol-3-yl)pyrimidin-2-yl)amino)phenyl)acrylamide methanesulfonate salt (formula 2) having a molar ratio of about 1:1 between methanesulfonic acid and free base, designated as Form 2B, having an X-ray powder diffraction pattern comprising three or more of the following 2θ values measured using CuKα radiation: 9.7°±0.2°, 12.8°±0.2°, 15.7°±0.2°, 18.2°±0.2°, 20.3°±0.2°, 25.1°±0.2°, 25.6°±0.2°, and 26.8°±0.2°

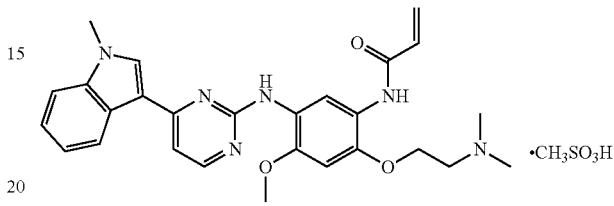

8. A crystalline form of N-(2-(2-(dimethylamino)ethoxy)-4-methoxy-5-((4-(1-methyl-1H-indol-3-yl)pyrimidin-2-yl)amino)phenyl)acrylamide hydrochloride salt (formula 3) having a molar ratio of about 1:1 between hydrochloride acid and free base, having an X-ray powder diffraction pattern comprising three or more of the following 2θ values measured using CuKα radiation: 8.5°±0.2°, 11.2°±0.2°, 18.1°±0.2°, 22.4°±0.2°, 23.5°±0.2°, and 26.3°±0.2°.

3

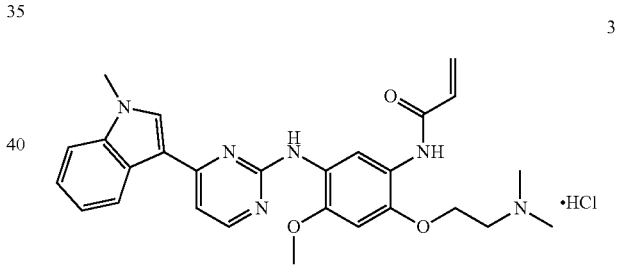

9. The crystalline form of claim 8, wherein the X-ray powder diffraction pattern further comprises two or more of the following 2θ values measured using CuKα radiation: 9.0°±0.2°, 12.7°±0.2°, 16.1°±0.2°, 17.3°±0.2°, 18.7°±0.2°, 20.6°±0.2°, 21.8°±0.2°, and 25.4°±0.2°.

10. The crystalline form of claim 8, having a melting point with an onset temperature at about 266.6° C. and/or a peak temperature at about 269.5° C. as measured by differential scanning calorimetry.

11. A crystalline form of N-(2-(2-(dimethylamino)ethoxy)-4-methoxy-5-((4-(1-methyl-1H-indol-3-yl)pyrimidin-2-yl)amino)phenyl)acrylamide sulfate salt (formula 4) having a molar ratio of about 1:1 between sulfuric acid and free base, having an X-ray powder diffraction pattern comprising three or more of the following 2θ values measured using CuKα radiation: 5.6°±0.2°, 7.3°±0.2°, 11.0°±0.2°, 11.9°±0.2°, 14.3°±0.2°, 18.1°±0.2°, 19.0°±0.2°, 19.6°±0.2°, 19.9°±0.2°, 22.2°±0.2°, 24.9°±0.2°, and 26.3°±0.2°.

14. The crystalline form of claim 13, having a melting point with an onset temperature at about 152.3° C. and/or a peak temperature at about 167.1° C. as measured by differential scanning calorimetry.

4

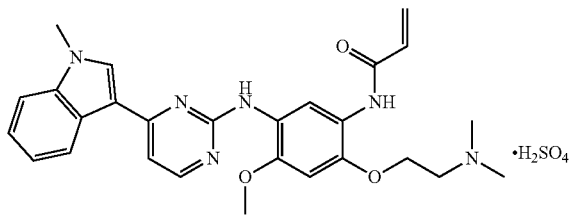

15. A crystalline form of N-(2-(2-(dimethylamino) ethoxy)-4-methoxy-5-((4-(1-methyl-1H-indol-3-yl)pyrimidin-2-yl)amino)phenyl)acrylamide citrate salt (formula 6) having a molar ratio of about 1:1 between citric acid and free base, having an X-ray powder diffraction pattern comprising three or more of the following 2θ values measured using CuKα radiation: 5.9°±0.2°, 8.0°±0.2°, 13.2°±0.2°, 19.0°±0.2°, 25.6°±0.2°, and 26.5°±0.2°.

6

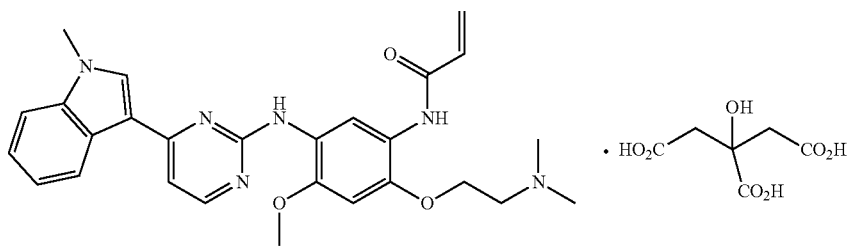

12. The crystalline form of claim 11, having a melting point with an onset temperature at about 152.3° C. and/or a peak temperature at about 167.1° C. as measured by differential scanning calorimetry.

13. A crystalline form of N-(2-(2-(dimethylamino) ethoxy)-4-methoxy-5-((4-(1-methyl-1H-indol-3-yl)pyrimidin-2-yl)amino)phenyl)acrylamide p-toluenesulfonate (p-tosylate) salt (formula 5) having a molar ratio of about 1:1 between p-toluenesulfonic acid and free base, having an X-ray powder diffraction pattern comprising three or more of the following 2θ values measured using CuKα radiation: 6.8°±0.2°, 7.3°±0.2°, 10.3°±0.2°, 11.3°±0.2°, 13.1°±0.2°, 15.6°±0.2°, 18.2°±0.2°, 20.5°±0.2°, 19.9°±0.2°, 22.7°±0.2°, 23.3°±0.2°, 27.1°±0.2°, and 29.7°±0.2°.

16. The crystalline form of claim 15, wherein the X-ray powder diffraction pattern further comprises two or more of the following 2θ values measured using CuKα radiation: 12.6°±0.2°, 16.0°±0.2°, 16.6°±0.2°, 17.0°±0.2°, 18.5°±0.2°, 20.3°±0.2°, 23.2°±0.2°, and 25.8°±0.2°.

17. A pharmaceutical composition comprising a crystalline form of claim 4, and a pharmaceutically acceptable carrier, adjuvant, diluent, and/or vehicle.

18. A pharmaceutical composition comprising a crystalline form of claim 1, and a pharmaceutically acceptable carrier, adjuvant, diluent, and/or vehicle.

19. A pharmaceutical composition comprising a crystalline form of claim 7, and a pharmaceutically acceptable carrier, adjuvant, diluent, and/or vehicle.

20. A pharmaceutical composition comprising a crystalline form of claim 8, and a pharmaceutically acceptable carrier, adjuvant, diluent, and/or vehicle.

21. A pharmaceutical composition comprising a crystalline form of claim 11, and a pharmaceutically acceptable carrier, adjuvant, diluent, and/or vehicle.

22. A pharmaceutical composition comprising a crystalline form of claim 13, and a pharmaceutically acceptable carrier, adjuvant, diluent, and/or vehicle.

23. A pharmaceutical composition comprising a crystalline form of claim 15, and a pharmaceutically acceptable carrier, adjuvant, diluent, and/or vehicle.

5

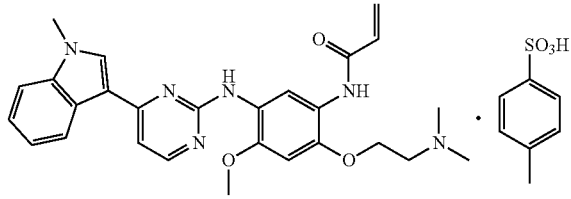

* * * * *